US008366655B2

(12) United States Patent
Kamen et al.

(10) Patent No.: US 8,366,655 B2
(45) Date of Patent: Feb. 5, 2013

(54) PERITONEAL DIALYSIS SENSOR APPARATUS SYSTEMS, DEVICES AND METHODS

(75) Inventors: Dean Kamen, Bedford, NH (US); N. Christopher Perry, Manchester, NH (US); Jason A. Demers, Manchester, NH (US); Brian Tracey, Litchfield, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 463 days.

(21) Appl. No.: 11/871,828

(22) Filed: Oct. 12, 2007

(65) Prior Publication Data

US 2008/0208111 A1   Aug. 28, 2008

Related U.S. Application Data

(60) Provisional application No. 60/921,314, filed on Apr. 2, 2007.

(51) Int. Cl.
*A61M 1/00* (2006.01)
*C02F 9/00* (2006.01)
(52) U.S. Cl. .......................................... 604/29; 210/258
(58) Field of Classification Search .................. 604/29, 604/64–67; 210/258
See application file for complete search history.

(56) References Cited

U.S. PATENT DOCUMENTS

| | | | |
|---|---|---|---|
| 3,200,648 A | 8/1965 | Waggaman | |
| 3,508,656 A * | 4/1970 | Serfass et al. | 210/90 |
| 3,656,873 A | 4/1972 | Schiff | |
| RE27,849 E | 12/1973 | Wortman | |
| 3,936,729 A | 2/1976 | Winslow | |
| 4,161,264 A | 7/1979 | Malmgren et al. | |
| 4,309,592 A * | 1/1982 | Le Boeuf | 392/470 |
| 4,479,760 A | 10/1984 | Bilstad et al. | |
| 4,479,761 A | 10/1984 | Bilstad et al. | |
| 4,664,891 A | 5/1987 | Cosentino et al. | |
| 4,680,445 A | 7/1987 | Ogawa | |

(Continued)

FOREIGN PATENT DOCUMENTS

| | | |
|---|---|---|
| DE | 3 328 744 A1 | 2/1985 |
| EP | 0 687 474 A1 | 12/1995 |

(Continued)

OTHER PUBLICATIONS

International Preliminary Report on Patentability for Application No. PCT/US2008/055000 mailed Sep. 11, 2009 and claims as pending for International Application No. PCT/US2008/055000 as of Sep. 11, 2009.

(Continued)

*Primary Examiner* — Kevin C Sirmons
*Assistant Examiner* — Bradley Osinski
(74) *Attorney, Agent, or Firm* — Wolf, Greenfield & Sacks, P.C.

(57) ABSTRACT

A sensor apparatus and sensor apparatus system for use in conjunction with a cassette-based peritoneal dialysis system is described, including a disposable cassette. In some embodiments, the cassette includes a thermal well for permitting the sensing of various properties of a dialysate. The thermal well includes a hollow housing of a thermally conductive material. In other embodiments, the cassette includes sensor leads for sensing of various properties of a dialysate. The thermal well has an inner surface shaped so as to form a mating relationship with a sensing probe. The mating thermally couples the inner surface with a sensing probe. In some embodiments, the thermal well is located on a disposable portion and the sensing probe on a reusable portion.

22 Claims, 42 Drawing Sheets

U.S. PATENT DOCUMENTS

| | | | |
|---|---|---|---|
| 4,927,411 A | 5/1990 | Pastrone et al. |
| 4,976,162 A | 12/1990 | Kamen |
| 5,062,774 A | 11/1991 | Kramer et al. |
| 5,088,515 A | 2/1992 | Kamen |
| 5,100,554 A | 3/1992 | Polaschegg |
| 5,110,477 A | 5/1992 | Howard et al. |
| 5,125,069 A | 6/1992 | O'Boyle |
| 5,206,522 A | 4/1993 | Danby et al. |
| 5,245,693 A | 9/1993 | Ford et al. |
| 5,247,434 A | 9/1993 | Peterson et al. |
| 5,267,956 A | 12/1993 | Beauchat |
| 5,274,245 A | 12/1993 | Lee |
| 5,278,072 A | 1/1994 | Wall et al. |
| 5,302,093 A | 4/1994 | Owens et al. |
| 5,306,242 A | 4/1994 | Joyce et al. |
| 5,324,422 A | 6/1994 | Colleran et al. |
| 5,326,476 A | 7/1994 | Grogan et al. |
| 5,350,357 A | 9/1994 | Kamen et al. |
| 5,378,126 A | 1/1995 | Abrahamson et al. |
| 5,381,510 A | 1/1995 | Ford et al. |
| 5,385,540 A | 1/1995 | Abbott et al. |
| 5,401,342 A | 3/1995 | Vincent et al. |
| 5,410,255 A | 4/1995 | Bailey |
| 5,421,823 A | 6/1995 | Kamen et al. |
| 5,429,485 A | 7/1995 | Dodge |
| 5,431,626 A | 7/1995 | Bryant et al. |
| 5,438,510 A | 8/1995 | Bryant et al. |
| 5,441,343 A | 8/1995 | Pylkki et al. |
| 5,474,683 A | 12/1995 | Bryant et al. |
| 5,482,440 A | 1/1996 | Dennehey et al. |
| 5,486,286 A | 1/1996 | Peterson et al. |
| 5,487,827 A | 1/1996 | Peterson et al. |
| 5,496,273 A | 3/1996 | Pastrone et al. |
| 5,542,919 A | 8/1996 | Simon et al. |
| 5,586,438 A | 12/1996 | Fahy |
| 5,593,290 A | 1/1997 | Greisch et al. |
| 5,628,908 A | 5/1997 | Kamen et al. |
| 5,634,896 A | 6/1997 | Bryant et al. |
| 5,638,737 A | 6/1997 | Mattson et al. |
| 5,645,531 A | 7/1997 | Thompson et al. |
| 5,680,111 A | 10/1997 | Danby et al. |
| 5,729,653 A | 3/1998 | Magliochetti et al. |
| 5,730,720 A | 3/1998 | Sites et al. |
| 5,747,824 A | 5/1998 | Jung et al. |
| 5,755,683 A | 5/1998 | Houle et al. |
| 5,875,282 A | 2/1999 | Jordan et al. |
| 5,899,873 A | 5/1999 | Jones et al. |
| 5,932,110 A | 8/1999 | Shah et al. |
| 5,938,634 A | 8/1999 | Packard |
| 5,947,931 A | 9/1999 | Bierman |
| 5,989,423 A | 11/1999 | Kamen et al. |
| 6,062,068 A | 5/2000 | Bowling |
| 6,070,761 A | 6/2000 | Bloom et al. |
| 6,101,406 A | 8/2000 | Hacker et al. |
| 6,136,201 A | 10/2000 | Shah et al. |
| 6,153,102 A | 11/2000 | Kenley et al. |
| 6,195,887 B1 | 3/2001 | Danby et al. |
| 6,210,361 B1 | 4/2001 | Kamen et al. |
| 6,223,130 B1 | 4/2001 | Gray et al. |
| 6,234,997 B1 | 5/2001 | Kamen et al. |
| 6,270,673 B1 | 8/2001 | Belt et al. |
| 6,302,653 B1 | 10/2001 | Bryant et al. |
| 6,331,778 B1 | 12/2001 | Dailey et al. |
| 6,336,911 B1 | 1/2002 | Westerbeck |
| 6,347,633 B1 | 2/2002 | Groth et al. |
| 6,382,923 B1 | 5/2002 | Gray |
| 6,406,426 B1 | 6/2002 | Reuss et al. |
| 6,406,452 B1 | 6/2002 | Westerbeck |
| 6,413,233 B1 | 7/2002 | Sites et al. |
| 6,415,797 B1 | 7/2002 | Groth et al. |
| 6,416,293 B1 | 7/2002 | Bouchard et al. |
| 6,468,241 B1 | 10/2002 | Gelfand et al. |
| 6,485,263 B1 | 11/2002 | Bryant et al. |
| 6,503,062 B1 | 1/2003 | Gray et al. |
| 6,517,510 B1 | 2/2003 | Stewart et al. |
| 6,579,253 B1 | 6/2003 | Burbank et al. |
| 6,595,944 B2 | 7/2003 | Balschat et al. |
| 6,660,974 B2 | 12/2003 | Faries, Jr. et al. |
| 6,673,314 B1 | 1/2004 | Burbank et al. |
| 6,709,417 B1 | 3/2004 | Houle et al. |
| 6,726,656 B2 | 4/2004 | Kamen et al. |
| 6,743,201 B1 | 6/2004 | Doing et al. |
| 6,749,403 B2 | 6/2004 | Bryant et al. |
| 6,750,468 B2 | 6/2004 | Malmstrom et al. |
| 6,752,172 B2 | 6/2004 | Lauer |
| 6,768,085 B2 | 7/2004 | Faries, Jr. et al. |
| 6,775,473 B2 | 8/2004 | Augustine et al. |
| 6,788,885 B2 | 9/2004 | Mitsunaga et al. |
| 6,806,947 B1 | 10/2004 | Ekdahl et al. |
| 6,814,547 B2 | 11/2004 | Childers et al. |
| 6,826,948 B1 | 12/2004 | Bhatti et al. |
| 6,860,866 B1 | 3/2005 | Graf et al. |
| 6,877,713 B1 | 4/2005 | Gray et al. |
| 6,905,479 B1 | 6/2005 | Bouchard et al. |
| 6,929,751 B2 | 8/2005 | Bowman, Jr. et al. |
| 6,949,079 B1 | 9/2005 | Westberg et al. |
| 7,083,719 B2 | 8/2006 | Bowman, Jr. et al. |
| 7,122,210 B2 | 10/2006 | Elisabettini et al. |
| 7,147,613 B2 | 12/2006 | Burbank et al. |
| 7,168,334 B1 | 1/2007 | Drott |
| 7,175,606 B2 | 2/2007 | Bowman, Jr. et al. |
| 7,238,164 B2 | 7/2007 | Childers et al. |
| 7,300,413 B2 | 11/2007 | Burbank et al. |
| 7,318,892 B2 | 1/2008 | Connell et al. |
| 7,327,273 B2 | 2/2008 | Hung et al. |
| 7,410,294 B2 * | 8/2008 | Shiraki et al. ............... 374/208 |
| 7,544,179 B2 | 6/2009 | Distler et al. |
| 7,632,078 B2 | 12/2009 | Demers et al. |
| 7,736,328 B2 | 6/2010 | Childers et al. |
| 7,794,141 B2 | 9/2010 | Perry et al. |
| 8,197,439 B2 | 6/2012 | Wang et al. |
| 2002/0056672 A1 | 5/2002 | Lyle et al. |
| 2002/0103453 A1 | 8/2002 | Burbank et al. |
| 2002/0150476 A1 | 10/2002 | Lucke et al. |
| 2002/0179595 A1 | 12/2002 | Nagele |
| 2003/0114795 A1 | 6/2003 | Faries et al. |
| 2003/0220599 A1 | 11/2003 | Lundtveit et al. |
| 2003/0220607 A1 | 11/2003 | Busby et al. |
| 2003/0229302 A1 | 12/2003 | Robinson et al. |
| 2004/0019313 A1 * | 1/2004 | Childers et al. ............... 604/5.01 |
| 2004/0091374 A1 | 5/2004 | Gray |
| 2004/0101026 A1 | 5/2004 | Nitta et al. |
| 2004/0138607 A1 | 7/2004 | Burbank et al. |
| 2005/0020958 A1 | 1/2005 | Paolini et al. |
| 2005/0069425 A1 | 3/2005 | Gray et al. |
| 2005/0095154 A1 | 5/2005 | Tracey et al. |
| 2005/0126998 A1 | 6/2005 | Childers |
| 2005/0130332 A1 | 6/2005 | Ishii et al. |
| 2005/0131332 A1 | 6/2005 | Kelly et al. |
| 2005/0230292 A1 | 10/2005 | Beden et al. |
| 2005/0274658 A1 | 12/2005 | Rosenbaum et al. |
| 2006/0093531 A1 | 5/2006 | Tremoulet et al. |
| 2006/0184084 A1 | 8/2006 | Ware et al. |
| 2006/0195064 A1 | 8/2006 | Plahey et al. |
| 2006/0241550 A1 | 10/2006 | Kamen et al. |
| 2006/0251533 A1 | 11/2006 | Nighy et al. |
| 2007/0060786 A1 | 3/2007 | Gura et al. |
| 2007/0112297 A1 | 5/2007 | Plahey et al. |
| 2007/0135758 A1 | 6/2007 | Childers et al. |
| 2007/0253463 A1 | 11/2007 | Perry et al. |
| 2007/0255527 A1 | 11/2007 | Schick et al. |
| 2008/0015493 A1 | 1/2008 | Childers et al. |
| 2008/0033346 A1 | 2/2008 | Childers et al. |
| 2008/0058697 A1 | 3/2008 | Kamen et al. |
| 2008/0058712 A1 | 3/2008 | Plahey |
| 2008/0077068 A1 | 3/2008 | Orr |
| 2008/0097283 A1 | 4/2008 | Plahey |
| 2008/0105600 A1 | 5/2008 | Connell et al. |
| 2008/0125693 A1 | 5/2008 | Gavin et al. |
| 2008/0132828 A1 | 6/2008 | Howard |
| 2008/0161751 A1 | 7/2008 | Plahey et al. |
| 2008/0175719 A1 | 7/2008 | Tracey et al. |
| 2008/0202591 A1 | 8/2008 | Grant et al. |
| 2008/0203023 A1 | 8/2008 | Burbank et al. |
| 2008/0205481 A1 | 8/2008 | Faries et al. |
| 2008/0208103 A1 | 8/2008 | Demers et al. |
| 2008/0208111 A1 | 8/2008 | Kamen et al. |

| | | | |
|---|---|---|---|
| 2008/0216898 A1 | 9/2008 | Grant et al. |
| 2008/0240929 A1 | 10/2008 | Kamen et al. |
| 2008/0253427 A1 | 10/2008 | Kamen et al. |
| 2008/0253911 A1 | 10/2008 | Demers et al. |
| 2008/0253912 A1 | 10/2008 | Demers et al. |
| 2009/0004033 A1 | 1/2009 | Demers et al. |
| 2009/0007642 A1 | 1/2009 | Busby et al. |
| 2009/0008331 A1 | 1/2009 | Wilt et al. |
| 2009/0009290 A1 | 1/2009 | Kneip et al. |
| 2009/0012447 A1 | 1/2009 | Huitt et al. |
| 2009/0012448 A1 | 1/2009 | Childers et al. |
| 2009/0012449 A1 | 1/2009 | Lee et al. |
| 2009/0012450 A1 | 1/2009 | Shah et al. |
| 2009/0012452 A1 | 1/2009 | Slepicka et al. |
| 2009/0012453 A1 | 1/2009 | Childers et al. |
| 2009/0012454 A1 | 1/2009 | Childers |
| 2009/0012455 A1 | 1/2009 | Childers et al. |
| 2009/0012456 A1 | 1/2009 | Childers et al. |
| 2009/0012457 A1 | 1/2009 | Childers et al. |
| 2009/0012458 A1 | 1/2009 | Childers et al. |
| 2009/0012460 A1 | 1/2009 | Steck et al. |
| 2009/0012461 A1 | 1/2009 | Childers et al. |
| 2009/0088675 A1 | 4/2009 | Kelly et al. |
| 2009/0095679 A1 | 4/2009 | Demers et al. |
| 2009/0101566 A1 | 4/2009 | Crnkovich et al. |
| 2009/0107902 A1 | 4/2009 | Childers et al. |
| 2009/0112151 A1 | 4/2009 | Chapman et al. |
| 2009/0113335 A1 | 4/2009 | Sandoe et al. |
| 2009/0114582 A1 | 5/2009 | Grant et al. |
| 2009/0137940 A1 | 5/2009 | Orr |
| 2009/0154524 A1 | 6/2009 | Girelli |
| 2009/0173682 A1 | 7/2009 | Robinson et al. |
| 2009/0192367 A1 | 7/2009 | Braig et al. |
| 2009/0222119 A1 | 9/2009 | Plahey et al. |
| 2009/0294359 A1 | 12/2009 | Hopping et al. |
| 2010/0056975 A1 | 3/2010 | Dale et al. |
| 2010/0116740 A1 | 5/2010 | Fulkerson et al. |
| 2010/0191180 A1 | 7/2010 | Childers et al. |
| 2010/0191181 A1 | 7/2010 | Childers et al. |
| 2010/0312162 A1 | 12/2010 | Masaoka et al. |
| 2011/0071465 A1 | 3/2011 | Wang et al. |
| 2011/0092893 A1 | 4/2011 | Demers et al. |
| 2011/0092894 A1 | 4/2011 | McGill et al. |
| 2011/0098635 A1 | 4/2011 | Helmore et al. |
| 2011/0105877 A1 | 5/2011 | Wilt et al. |
| 2011/0106002 A1 | 5/2011 | Helmore et al. |
| 2011/0125085 A1 | 5/2011 | McGill et al. |
| 2011/0218600 A1 | 9/2011 | Kamen et al. |
| 2012/0123322 A1 | 5/2012 | Scarpaci et al. |
| 2012/0207627 A1 | 8/2012 | Demers et al. |

FOREIGN PATENT DOCUMENTS

| | | |
|---|---|---|
| EP | 0 815 882 A2 | 1/1998 |
| EP | 0 829 266 A2 | 3/1998 |
| EP | 0 992 255 A2 | 4/2000 |
| EP | 2 131 893 A1 | 12/2009 |
| EP | 2 335 753 A1 | 6/2011 |
| GB | 2 423 241 A | 8/2006 |
| WO | WO 94/20158 A1 | 9/1994 |
| WO | WO 98/37801 A1 | 9/1998 |
| WO | WO 99/02206 A1 | 1/1999 |
| WO | WO 99/10028 A1 | 3/1999 |
| WO | WO 00/15278 A1 | 3/2000 |
| WO | WO 01/37895 A2 | 5/2001 |
| WO | WO 03/080268 A1 | 10/2003 |
| WO | WO 2004/041081 A1 | 5/2004 |
| WO | WO 2005/016443 A1 | 2/2005 |
| WO | WO 2005/044339 A1 | 5/2005 |
| WO | WO 2006/120415 A1 | 11/2006 |
| WO | WO 2007/120812 A2 | 10/2007 |
| WO | WO 2007/126360 A1 | 11/2007 |
| WO | WO 2008/106191 A2 | 9/2008 |
| WO | WO 2008/106440 A1 | 9/2008 |
| WO | WO 2008/106452 A1 | 9/2008 |
| WO | WO 2008/106538 A2 | 9/2008 |
| WO | WO 2009/006496 A1 | 1/2009 |
| WO | WO 2009/044221 A1 | 4/2009 |
| WO | WO 2009/051669 A1 | 4/2009 |
| WO | WO 2009/094179 A2 | 7/2009 |
| WO | WO 2009/094182 A2 | 7/2009 |
| WO | WO 2009/094183 A1 | 7/2009 |
| WO | WO 2009/094184 A1 | 7/2009 |
| WO | WO 2009/094185 A2 | 7/2009 |
| WO | WO 2009/094186 A2 | 7/2009 |
| WO | WO 2012/006425 A2 | 1/2012 |

OTHER PUBLICATIONS

International Preliminary Report on Patentability for Application No. PCT/US2008/055168 mailed Sep. 11, 2009 and claims as pending for International Application No. PCT/US2008/055168 as of Sep. 11, 2009.

International Preliminary Report on Patentability for Application No. PCT/US2008/055021 mailed Sep. 11, 2009 and claims as pending for International Application No. PCT/US2008/055021 as of Sep. 11, 2009.

International Search Report and Written Opinion for Application No. PCT/US2008/055000 mailed Aug. 1, 2008 and claims as pending for International Application No. PCT/US2008/055000 as of Aug. 1, 2008.

International Search Report and Written Opinion for Application No. PCT/US2008/055168 mailed Nov. 10, 2008 and claims as pending for International Application No. PCT/US2008/055168 as of Nov. 10, 2008.

International Search Report and Written Opinion for Application No. PCT/US2008/011663 mailed Feb. 20, 2009 and claims as pending for International Application No. PCT/US2008/011663 as of Feb. 20, 2009.

International Search Report and Written Opinion for Application No. PCT/US2008/055021 mailed Jul. 23, 2008 and claims as pending for International Application No. PCT/US2008/055021 as of Jul. 23, 2008.

Invitation to Pay Additional Fees for Application No. PCT/US2008/055168 mailed Aug. 5, 2008 and claims as pending for International Application No. PCT/US2008/055168 as of Aug. 5, 2008.

Notice of Allowance for U.S. Appl. No. 11/787,112, filed Apr. 13, 2007, published as US 2007-0253463 on Nov. 1, 2007, which Notice of Allowance is dated Jun. 30, 2009, and claims as allowed for U.S. Appl. No. 11/787,112 as of Jun. 30, 2009.

Notice of Allowance for U.S. Appl. No. 11/787,112, filed Apr. 13, 2007, published as US 2007-0253463 on Nov. 1, 2007, which Notice of Allowance is dated Jan. 12, 2010, and claims as allowed for U.S. Appl. No. 11/787,112 as of Jan. 12, 2010.

Notice of Allowance for U.S. Appl. No. 11/787,112, filed Apr. 13, 2007, published as US 2007-0253463 on Nov. 1, 2007, which Notice of Allowance is dated Apr. 29, 2010, and claims as allowed for U.S. Appl. No. 11/787,112 as of Apr. 29, 2010.

Notice of Allowance for U.S. Appl. No. 11/787,112, filed Apr. 13, 2007, published as US 2007-0253463 on Nov. 1, 2007, which Notice of Allowance is dated Jul. 19, 2010.

Office Action for U.S. Appl. No. 11/787,112, filed Apr. 13, 2007, published as US 2007-0253463 on Nov. 1, 2007, which Office Action is dated Nov. 21, 2008, and claims as pending for U.S. Appl. No. 11/787,112 as of Nov. 21, 2008.

Office Action for U.S. Appl. No. 11/871,821, filed Oct. 12, 2007, published as US 2008-0240929 on Oct. 2, 2008, which Office Action is dated Sep. 23, 2009, and claims as pending for U.S. Appl. No. 11/871,821 as of Sep. 23, 2009.

International Search Report and Written Opinion for Application No. PCT/US2008/055136 mailed Jul. 24, 2008.

International Preliminary Report on Patentability for Application No. PCT/US2008/055136 mailed Sep. 11, 2009.

International Search Report and Written Opinion for Application No. PCT/US2009/000439 mailed Jun. 3, 2009.

International Preliminary Report on Patentability for Application No. PCT/US2009/000439 mailed Aug. 5, 2010.

Invitation to Pay Additional Fees for Application No. PCT/US2009/000436 mailed Jun. 4, 2009.

International Search Report and Written Opinion for Application No. PCT/US2009/000436 mailed Sep. 25, 2009.

International Preliminary Report on Patentability for Application No. PCT/US2009/000436 mailed Aug. 5, 2010.

Invitation to Pay Additional Fees for Application No. PCT/US2009/000440 mailed Jun. 4, 2009.
International Search Report and Written Opinion for Application No. PCT/US2009/000440 mailed Sep. 25, 2009.
International Preliminary Report on Patentability for Application No. PCT/US2009/000440 mailed Aug. 5, 2010.
Invitation to Pay Additional Fees for Application No. PCT/US2009/000433 mailed Jun. 4, 2009.
International Search Report and Written Opinion for Application No. PCT/US2009/000433 mailed Sep. 25, 2009.
International Preliminary Report on Patentability for Application No. PCT/US2009/000433 mailed Aug. 5, 2010.
Extended European Search Report for EP Application No. 10192384.5 filed Jan. 23, 2009, published as EP 2335753 on Jun. 22, 2011, which Extended European Search Report is dated May 6, 2011, and claims as pending for EP Application No. 10192384.5 as of May 6, 2011.
International Search Report and Written Opinion for Application No. PCT/US2009/000437 mailed Jun. 3, 2009.
International Preliminary Report on Patentability for Application No. PCT/US2009/000437 mailed Aug. 5, 2010.
Invitation to Pay Additional Fees for Application No. PCT/US2009/000441 mailed Jun. 24, 2009.
International Search Report and Written Opinion for Application No. PCT/US2009/000441 mailed Oct. 2, 2009.
International Preliminary Report on Patentability for Application No. PCT/US2009/000441 mailed Aug. 5, 2010.
Examination Report for EP Application No. 08730761.7 filed Feb. 26, 2008, publsihed as EP 2131893 on Dec. 16, 2009, which Examination Report is dated Sep. 23, 2011, and claims as pending for EP Application No. 08730761.7 as of Sep. 23, 2011.
Invitation to Pay Additional Fees for PCT/US2011/043196 mailed Nov. 7, 2011.
Office Action for U.S. Appl. No. 11/787,213, filed Apr. 13, 2007, published as 2008-0058697 on Mar. 6, 2008, which Office Action is dated Mar. 18, 2010, and claims as pending for U.S. Appl. No. 11/787,213 as of Mar. 18, 2010.
Office Action for AU Application No. 2008231167 filed Feb. 27, 2008, unpublished as of Sep. 5, 2012, which Office Action is dated Jul. 30, 2012, and claims as pending for AU Application No. 2008231167 as of Jul. 30, 2012.
Examination Report for EP Application No. 08730848.2 filed Feb. 27, 2008, published as EP 2131890 on Dec. 16, 2009, which Examination Report is dated Dec. 30, 2011, and claims as pending for EP Application No. 08730848.2 as of Dec. 30, 2011.
Examination Report for EP Application No. 07755392.3 filed Apr. 13, 2007, published as EP 2 010 247 on Jan. 7, 2009, which Examination Report is dated Sep. 7, 2011, and claims as pending for EP Application No. 07755392.3 as of Sep. 7, 2011.
Written Opinion for Application No. PCT/US2007/009107 mailed Aug. 17, 2007.
International Preliminary Report on Patentability for Application No. PCT/US2007/009107 mailed Oct. 23, 2008.
International Search Report and Written Opinion for PCT/US2011/043196 mailed Feb. 17, 2012.
Office Action for U.S. Appl. No. 11/871,787, filed Oct. 12, 2007, published as US 2008-0253911 on Oct. 16, 2008, which Office Action is dated Apr. 14, 2011, and claims as pending for U.S. Appl. No. 11/871,787 as of Apr. 14, 2011.
Office Action for U.S. Appl. No. 12/038,474, filed Feb. 27, 2008, published as US 2008-0253427 on Oct. 16, 2008, which Office Action is dated Feb. 7, 2011, and claims as pending for U.S. Appl. No. 12/038,474 as of Feb. 7, 2011.
Office Action for U.S. Appl. No. 12/038,474, filed Feb. 27, 2008, published as US 2008-0253427 on Oct. 16, 2008, which Office Action is dated Sep. 1, 2011, and claims as pending for U.S. Appl. No. 12/038,474 as of Sep. 1, 2011.
Office Action for U.S. Appl. No. 12/038,474, filed Feb. 27, 2008, published as US 2008-0253427 on Oct. 16, 2008, which Office Action is dated May 15, 2012, and claims as pending for U.S. Appl. No. 12/038,474 as of May 15, 2012.
Office Action for U.S. Appl. No. 12/730,197, filed Mar. 23, 2010, published as US 2010-0327849 on Dec. 30, 2010, which Office Action is dated Nov. 17, 2011, and claims as pending for U.S. Appl. No. 12/730,197 as of Nov. 17, 2011.
Notice of Allowance for U.S. Appl. No. 12/730,197, filed Mar. 23, 2010, published as US 2010-0327849 on Dec. 30, 2010, which Notice of Allowance is dated May 3, 2012, and claims as allowed for U.S. Appl. No. 12/730,197 as of May 3, 2012.
MIRSA, The basics of hemodialysis equipment. Hemodial Int. Jan 2005;9(1):30-6.
Smith, Temperature Correction in Conductivity Measurements. Limnology and Oceanography. 1962;7(3):330-334.

* cited by examiner

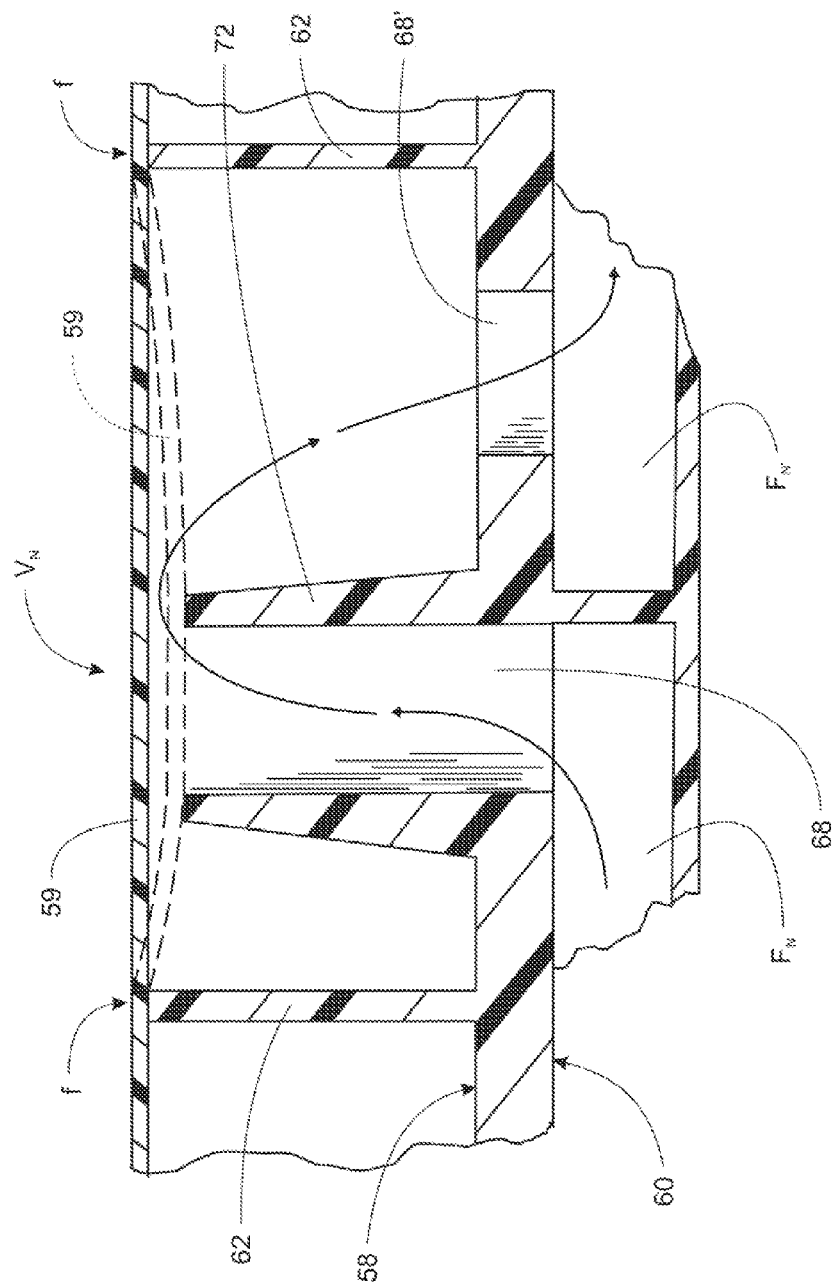

PERITONEAL DIALYSIS SENSOR APPARATUS SYSTEMS, DEVICES AND METHODS

CROSS-REFERENCE TO RELATED APPLICATIONS

This application claims priority from the following U.S. Provisional Patent Applications, all of which are hereby incorporated herein by reference in their entireties:

U.S. Provisional Patent Application No. 60/904,024 entitled Hemodialysis System and Methods filed on Feb. 27, 2007; and U.S. Provisional Patent Application No. 60/921,314 entitled Sensor Apparatus filed on Apr. 2, 2007.

This application is also related to U.S. patent application Ser. No. 11/871,821, published as U.S. Patent Application Publication No. 2008/0240929 entitled Sensor Apparatus Systems, Devices and Methods, which is hereby incorporated herein by reference in its entirety.

TECHNICAL FIELD

The present invention relates to sensor systems, devices, and methods, and more particularly to peritoneal dialysis systems, devices, and methods for sensors, sensor apparatus, and sensor apparatus systems.

BACKGROUND ART

Peritoneal Dialysis (PD) periodically infuses sterile aqueous solution into the peritoneal cavity. This solution is called peritoneal dialysis solution, or dialysate. Diffusion and osmosis exchanges take place between the solution and the bloodstream across the natural body membranes. These exchanges remove the waste products that the kidneys normally excrete. The waste products typically consist of solutes like sodium and chloride ions, and the other compounds normally excreted through the kidneys like urea, creatinine, and water.

Automated Peritoneal Dialysis (APD) is a popular form of PD. APD uses a machine, called a cycler, to automatically infuse, dwell, and drain peritoneal dialysis solution, or dialysate, to and from the patient's peritoneal cavity. A typical APD sequence lasts for several hours. It often begins with an initial drain cycle to empty the peritoneal cavity of spent dialysate. The APD sequence then proceeds through a succession of fill, dwell, and drain phases that follow one after the other. Each fill/dwell/drain sequence is called a cycle. During the fill phase, the cycler transfers a predetermined volume of fresh, warmed dialysate into the peritoneal cavity of the patient. The dialysate remains (or "dwells") within the peritoneal cavity for a time. This is called the dwell phase. During the drain phase, the cycler removes the spent dialysate from the peritoneal cavity. The number of fill/dwell/drain cycles that are required during a given APD session depends upon the total volume of dialysate prescribed for the patient's APD regime.

Systems for performing peritoneal dialysis are known in the art. U.S. Pat. No. 5,350,357, entitled Peritoneal Dialysis Systems Employing a Liquid Distribution and Pumping Cassette that Emulates Gravity, and other patents, describe a cassette-based peritoneal dialysis system. PD systems of the type described in U.S. Pat. No. 5,350,357 have been very well received by professionals and patients for the treatment of end-stage renal disease.

Despite the success of such peritoneal dialysis systems, there is a need for sensor apparatus and sensor apparatus systems capable of sensing the temperature, the conductivity, and/or other properties of the dialysate present in the cassette.

Additionally, there is a need for an accurate measurement apparatus to measure the temperature, conductivity, and/or other property of the dialysate in the cassette while avoiding contamination between with the measurement apparatus and the dialysate. There is also a need for an accurate measurement apparatus that can measure the temperature, conductivity, and/or other condition of a dialysate where such dialysate is contained in and/or flowing through a disposable cassette such that part or all of the sensor apparatus can be reused and need not be disposed of along with the disposable cassette.

SUMMARY OF THE INVENTION

In accordance with one aspect of the invention there is provided a system for performing peritoneal dialysis including a sensor apparatus system for determining one or more properties of dialysate solution in a cassette, the system comprising a peritoneal dislysis cycler; a thermal sensor in said cycler having a sensing end and a connector end; a probe tip thermally coupled to said sensing end of the thermal sensor and attached to said cycler, the probe tip adapted for thermal coupling with an inner surface of a well installed in the cassette; and at least two leads connected to said connector end of said thermal sensor, whereby thermal energy is transferred from said well to said thermal sensor and whereby temperature information is conveyed through said leads. In various alternative embodiments, the sensing probe may further include a third lead attached to one of the probe housing, the thermal sensor, and the probe tip for permitting conductivity sensing. Alternatively, the sensing probe may further include a conductivity sensor attached to one of the probe housing, the thermal sensor, and the probe tip for permitting conductivity sensing; and a third lead attached to the conductivity sensor for transmitting conductivity information. A urethane resin may be included between said probe tip and said probe housing. The probe tip may include a flange for mating with the housing.

In various alternative embodiments of the sensor apparatus system described above, thermal epoxy may be included between said thermal sensor and said probe tip. The probe tip may be copper, steel, or a metal including at least one of silver, copper, steel, and stainless steel. In various embodiments, the housing may be plastic or metal. The housing may include a flange disposed about said probe housing, and a spring may be used in conjunction with the flange. The housing may include an integrated flexible member.

Some embodiments of this aspect of the present invention include a well of a predetermined size and shape. The well mates with the probe and the probe tip is thermal coupled to said well.

In accordance with one aspect of the present invention the well includes a hollow housing of a thermally conductive material. The housing has an outer surface and an inner surface. The inner surface is a predetermined shape so as to form a mating relationship with a sensing probe. The mating thermally couples the inner surface with a sensing probe.

Some embodiments of this aspect of the present invention include a predetermined volume of thermal grease on the inner surface of the well.

In accordance with one aspect of the present invention, method for determining temperature and/or conductivity of a dialysate in a cassette is described. The method includes the following steps: installing at least one well in a cassette; thermally coupling a well and a sensing probe such that temperature and conductivity can be determined; transferring thermal and conductivity signals through at least 3 leads from the sensing probe; and determining temperature and conductivity using the signals.

In accordance with another aspect of the invention there is provided a cassette for performing peritoneal dialysis, wherein such cassette includes a thermal well in a fluid path for at least one of transmitting temperature and permitting conductivity sensing of fluid passing through the conduit, wherein the well is adapted for interconnection with a sensor.

In various alternative embodiments, the apparatus may be configured so that a portion of the well comes into contact with fluid in the conduit or so that no portion of the well comes into contact with fluid in the conduit. The fluid conduit in the cassette may include plastic tubing or metal tubing.

In various embodiments, the cassette containing the fluid path comprises a rigid body overlaid on one or more sides with a flexible diaphragm. In various embodiments the flexible diaphragm cassette includes one or more pump chambers and/or one or more value stations. In various embodiments, one or more thermal wells are positioned on the edge of the cassette. In certain of these embodiments, one or more wells are positioned on the bottom edge of the cassette.

The cassette and the well may be integrally formed from the same material.

Alternatively, the well may be coupled to the cassette, e.g., using at least one of press fit connection, flexible tabs, adhesive, ultrasonic weld, and a retaining plate and fastener. An o-ring may be disposed between the well and the fluid conduit. The o-ring may include one of a round cross-section, a square cross-section, and an X-shaped cross-section. The well may include a groove to receive a portion of the o-ring. A portion of the well in contact with the conduit may be flexible so as to deform the conduit and may include a plurality of cuts to provide such flexibility.

In accordance with another aspect of the invention there is provided a fluid pumping cassette comprising at least one pump chamber, one valve station, and one thermal well for at least one of transmitting temperature and permitting conductivity sensing of fluid passing through the conduit, wherein the well is adapted for interconnection with a sensor.

In accordance with another aspect of the invention there is provided a sensing system comprising at least one sensing probe and at least one well installed in a cassette, the well in communication with the sensing probe for at least one of thermal sensing and conductivity sensing.

These aspects of the invention are not meant to be exclusive or comprehensive and other features, aspects, and advantages of the present invention are possible and will be readily apparent to those of ordinary skill in the art when read in conjunction with the following description, the appended claims, and the accompanying drawings.

BRIEF DESCRIPTION OF THE DRAWINGS

The foregoing features of the invention will be more readily understood by reference to the following detailed description, taken with reference to the accompanying drawings, wherein:

FIG. 6C is an enlarged side section view of a typical cassette valve station shown in FIG. 6B;

It should be noted that the foregoing figures and the elements depicted therein are not necessarily drawn to consistent scale or to any scale. Unless the context otherwise suggests, like elements are indicated by like numerals.

DETAILED DESCRIPTION OF SPECIFIC EMBODIMENTS

Various aspects of the present invention are described below with reference to various exemplary embodiments. It should be noted that headings are included for convenience and do not limit the present invention in any way.

1. Pertinoneal Dialysis Utilizing a Cassette-Based System

Figure 1:
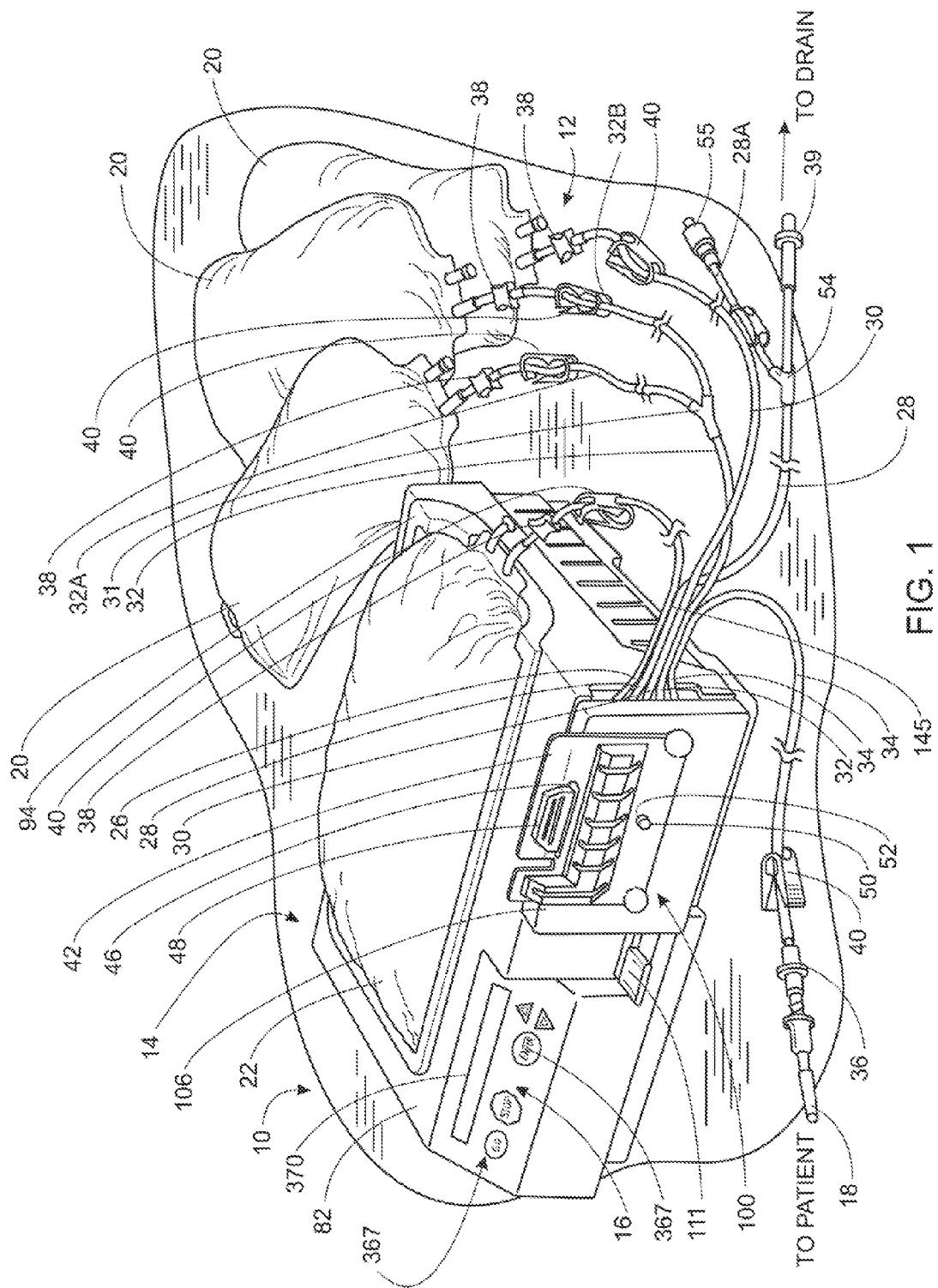
FIG. 1 is a perspective view an exemplary cassette-based automated peritoneal dialysis system.

FIG. 1 shows an exemplary cassette-based automated peritoneal dialysis system 10. The system 10 includes three principal components. These are a set 12 (including a cassette); a cycler 14 (shown in FIGS. 1 and 2) that interacts with the cassette to pump liquid; and a controller 16 that governs the interaction to perform a selected APD procedure. In the illustrated and preferred embodiment, the cycler and controller are located within a common housing 82.

Figure 2:
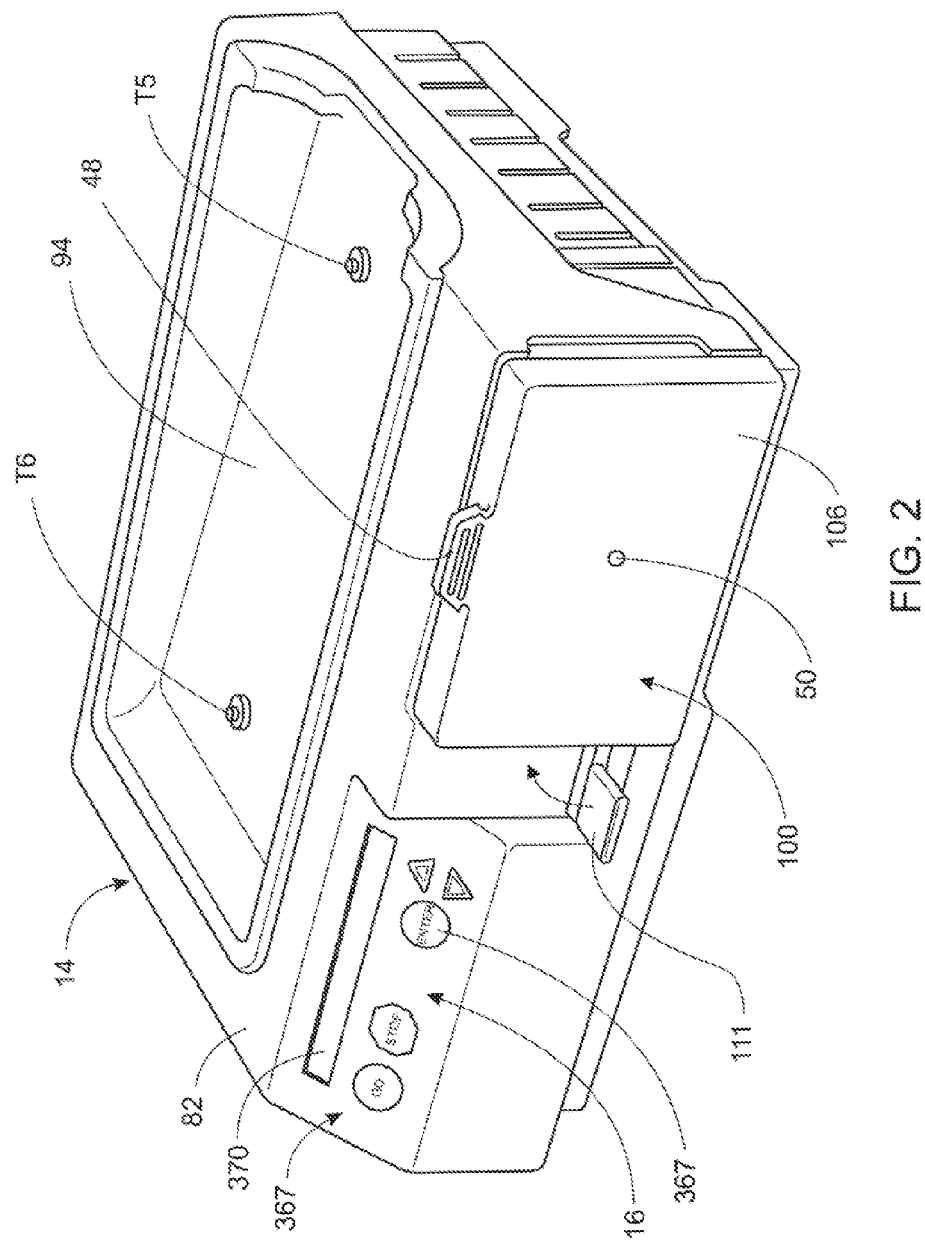
FIG. 2 is a perspective view of the cycler associated with the system shown in FIG. 1.

The cycler 14 is intended to be a durable item capable of long term, maintenance free use. As FIG. 2 shows, the cycler 14 also presents a compact footprint, suited for operation upon a table top or other relatively small surface normally found in the home. The cycler 14 is also lightweight and portable.

The set 12 is intended to be a single use, disposable item. The user loads the set 12 on the cycler 14 before beginning each APD therapy session. The user removes the set 12 from the cycler 14 upon the completing the therapy session and discards it.

In use (as FIG. 1 shows), the user connects the set 12 to his/her indwelling peritoneal catheter 18. The user also connects the set 12 to individual bags 20 containing sterile dialysis solution for infusion. The set 12 also connects to a bag 22 in which the dialysis solution is heated to a desired temperature (typically to about 37 degrees C.) before infusion.

Alternatively, as described in more detail below, the set may be connected to other sources of dialysate. For example, the set may be connected to a bag that contains two or more components that are separately stored from each other, such as in a multi-chamber container, until the components are mixed together to form the dialysate. In other embodiments, the set may be connected to a system for preparing dialysate. The system may prepare all or substantially all of the dialysate necessary for a complete PD treatment in one batch, may prepare the dialysate in a number of smaller batches, or may prepare the dialysate in real time or close to real time to its use.

The controller 16 paces the cycler 14 through a prescribed series of fill, dwell, drain cycles typical of an APD procedure. During the fill phase, the cycler 14 infuses the heated dialysate through the set 12 and into the patient's peritoneal cavity.

Following the dwell phase, the cycler 14 institutes a drain phase, during which the cycler 14 discharges spent dialysis solution from the patient's peritoneal cavity through the set into a nearby drain (not shown).

Figure 3:
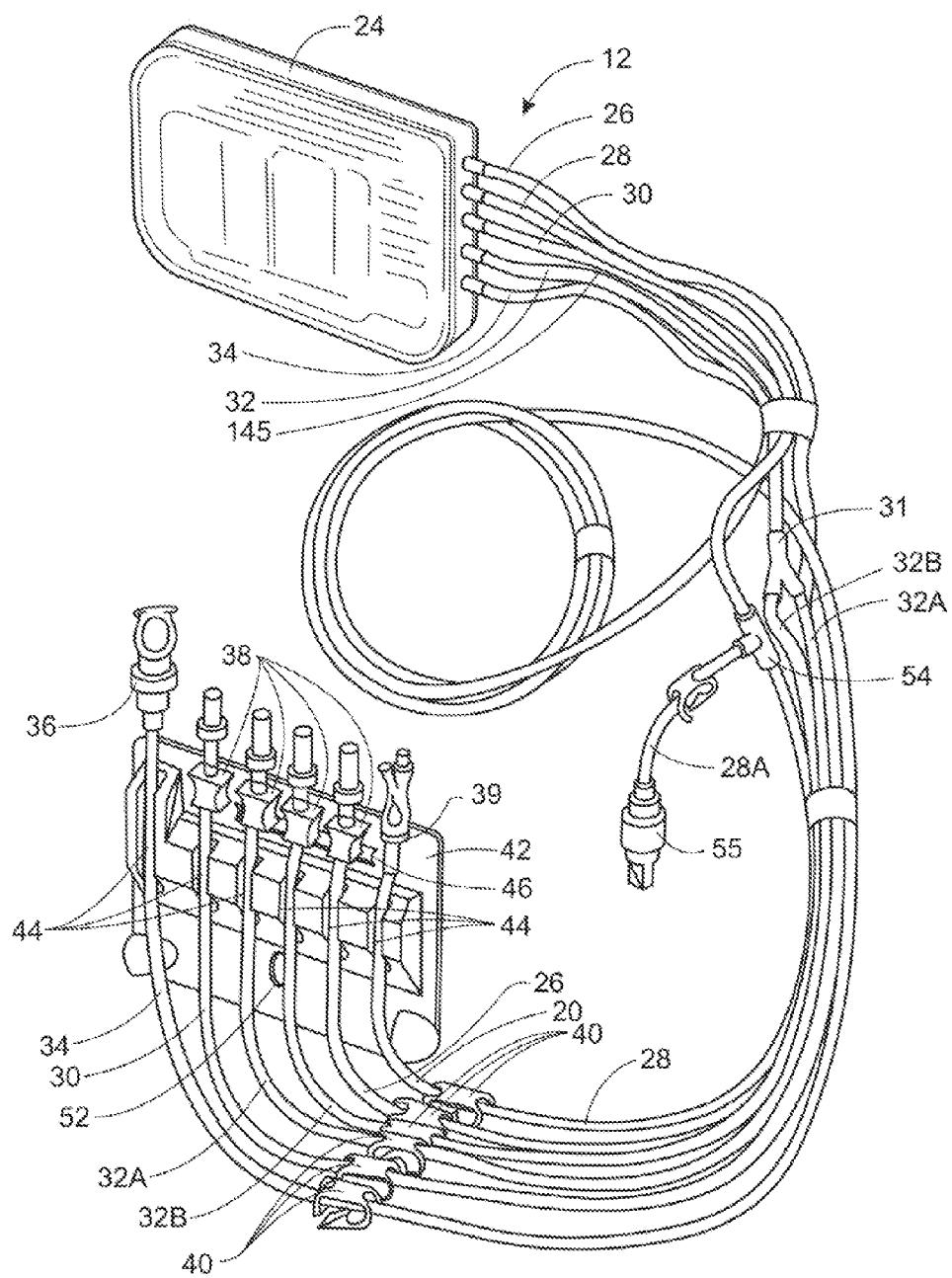
FIG. 3 is a perspective view of the cassette and the associated disposable liquid delivery set associated with the system shown in FIG. 1.

As FIG. 3 best shows, the set 12 includes a cassette 24 to which lengths of flexible plastic tubes 26/28/30/32/34 are attached.

The cassette 24 serves in association with the cycler 14 and the controller 16 to direct liquid flow among the multiple liquid sources and destinations that a typical APD procedure requires. As will be described in greater detail later, the cassette 24 provides centralized valving and pumping functions in carrying out the selected APD therapy.

Figure 6:
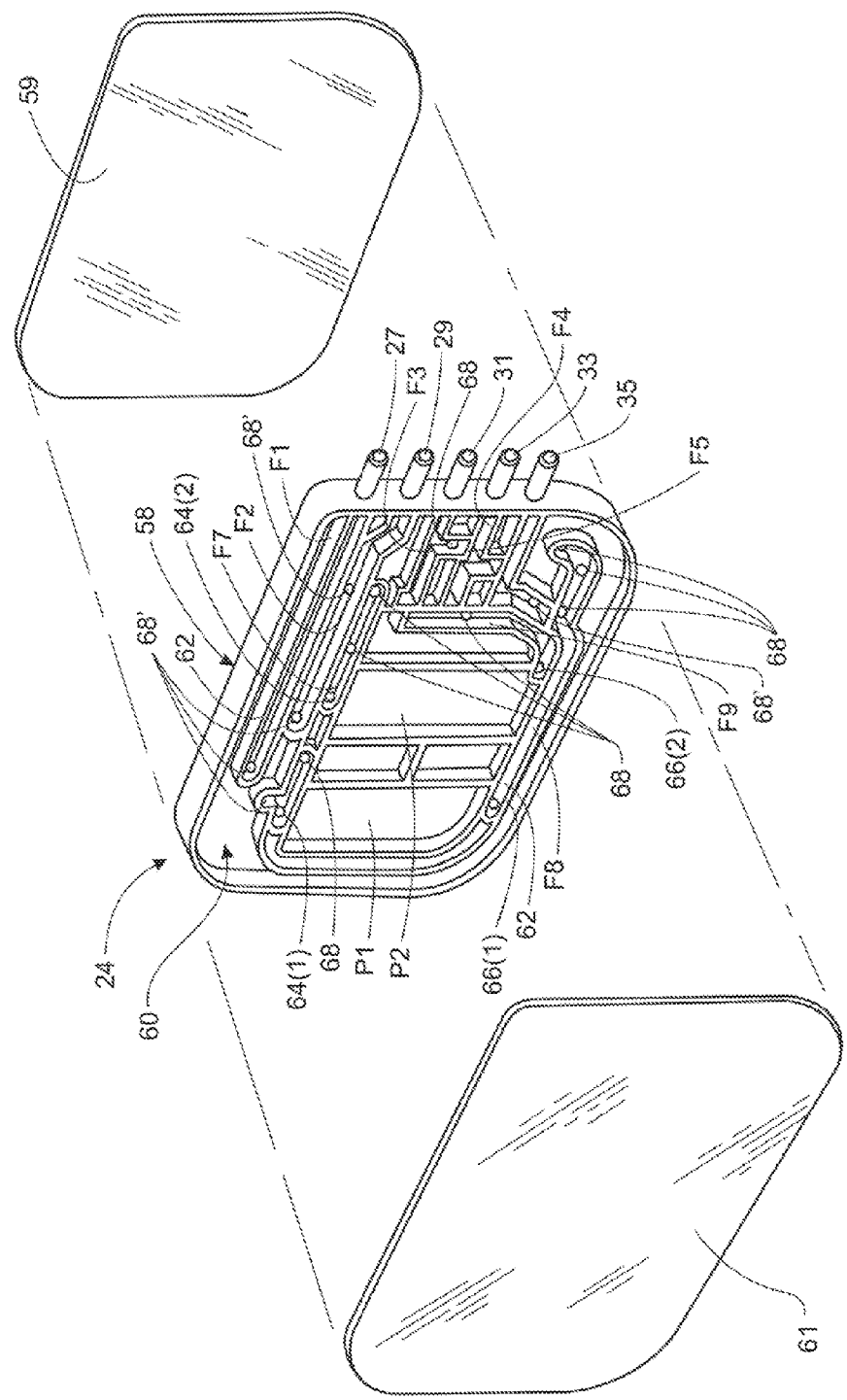
FIG. 6 is an exploded perspective view of one side of the cassette attached to the disposable set shown in FIG. 3.
Figure 6A:
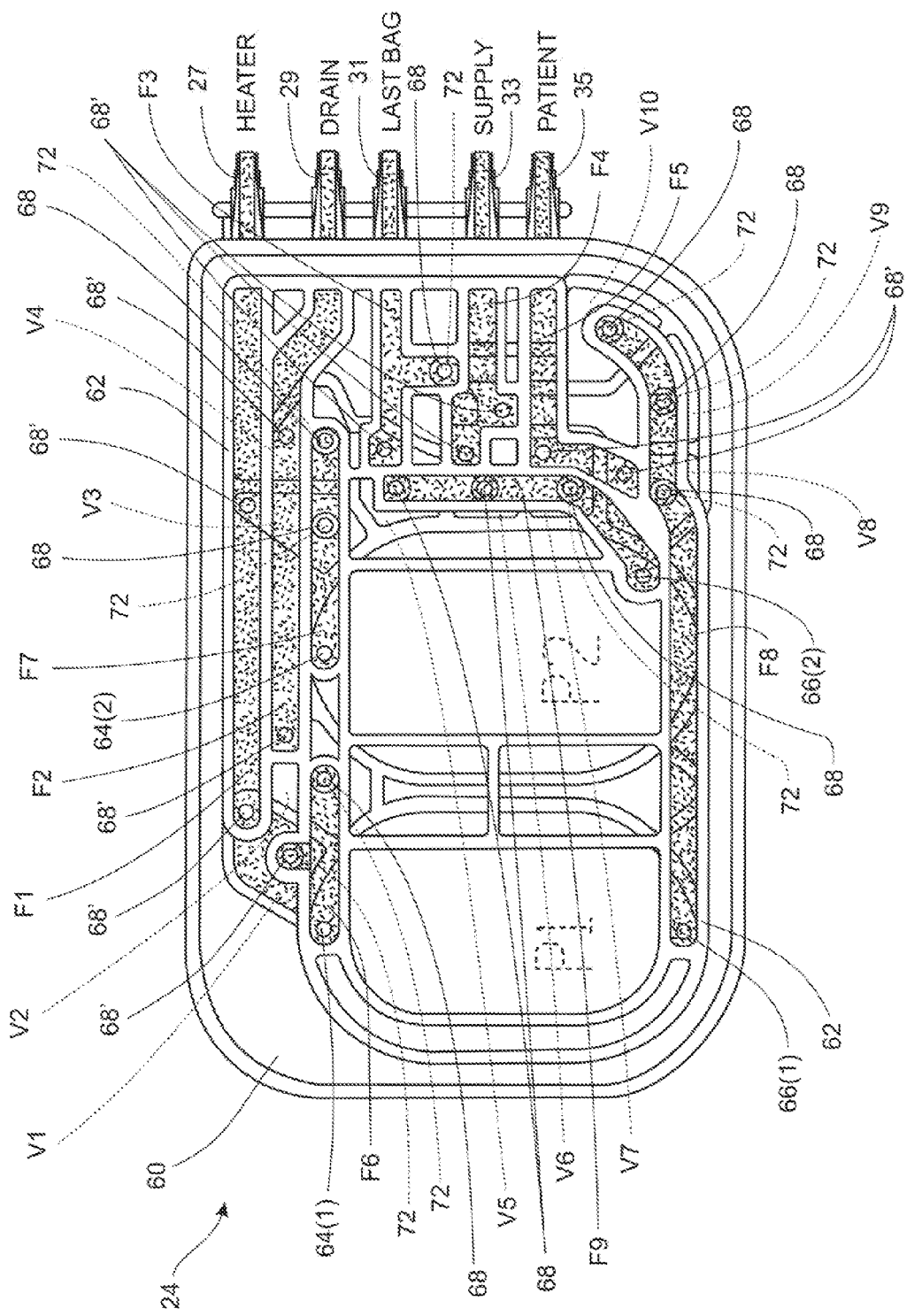
FIG. 6A is a plan view of the one side of the cassette shown in FIG. 6, showing the liquid paths within the cassette.
Figure 6B:
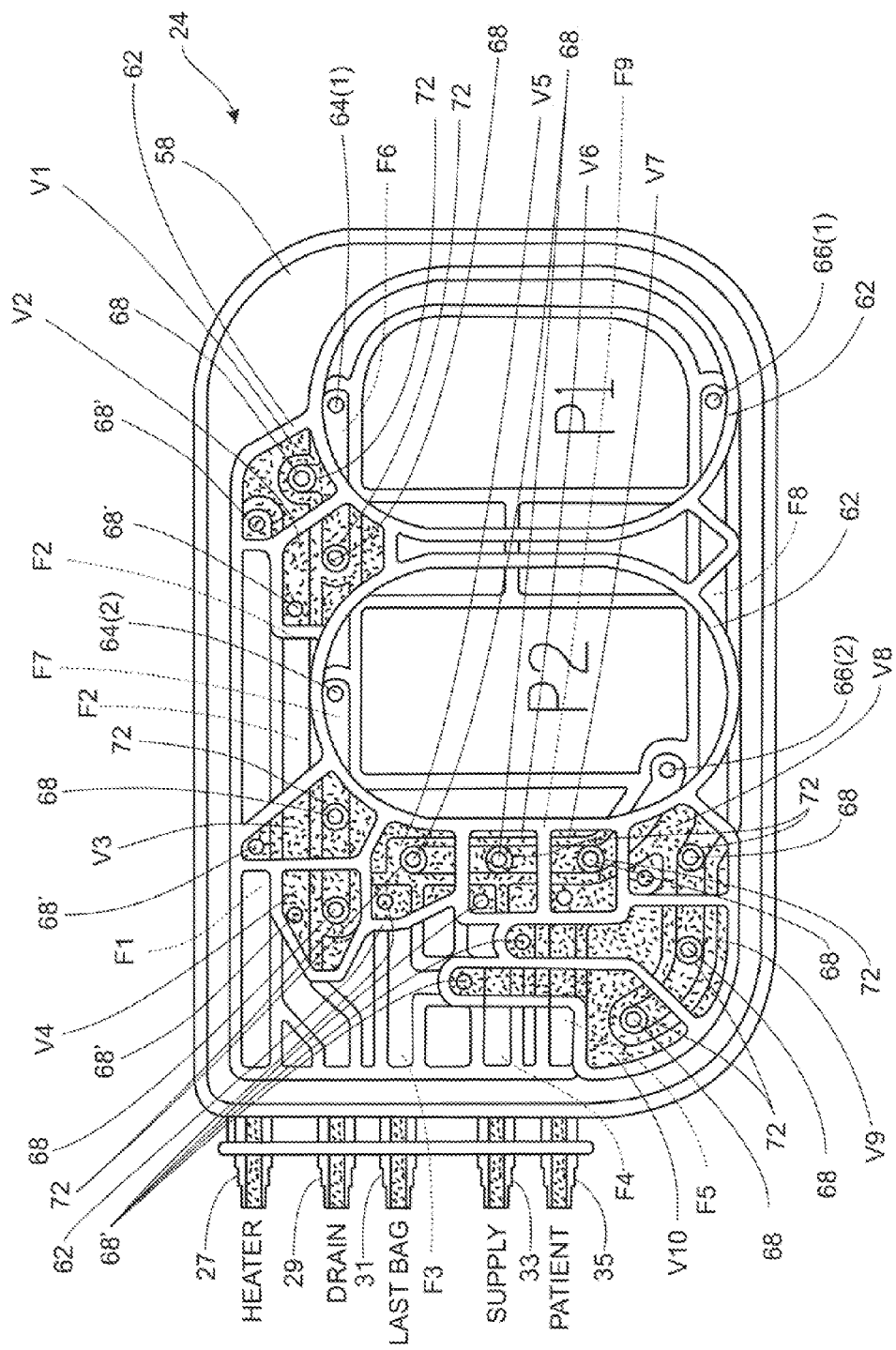
FIG. 6B is a plan view of the other side of the cassette shown in FIG. 6, showing the pump chambers and valve stations within the cassette.

FIGS. 6, 6A and 6B show the details of the cassette 24. As FIG. 6 shows, the cassette 24 includes an injection molded body having front and back sides 58 and 60. For the purposes of description, the front side 58 is the side of the cassette 24 that, when the cassette 24 is mounted in the holder 100, faces away from the user.

A flexible diaphragm 59 and 61 overlies the front side and back sides 58 and 60 of the cassette 24, respectively.

The cassette 24 is preferably made of a rigid medical grade plastic material. The diaphragms 59/61 are preferably made of flexible sheets of medical grade plastic. The diaphragms 59/61 are sealed about their peripheries to the peripheral edges of the front and back sides 58/60 of the cassette 24.

The cassette 24 forms an array of interior cavities in the shapes of wells and channels. The interior cavities create multiple pump chambers P1 and P2 (visible from the front side 58 of the cassette 24, as FIG. 6B shows). The interior cavities also create multiple paths F1 to F9 to convey liquid (visible from the back side 60 of the cassette 24, as FIGS. 6 and 6A shows). The interior cavities also create multiple valve stations V1 to V10 (visible from the front side 58 of the cassette 24, as FIG. 6B shows). The valve stations V1 to V10 interconnect the multiple liquid paths F1 to F9 with the pump chambers P1 and P2 and with each other.

The number and arrangement of the pump chambers, liquid paths, and valve stations can vary.

A typical APD therapy session usually requires five liquid sources/destinations. The cassette 24 that embodies the features of the invention provides these connections with five exterior liquid lines (i.e., the flexible tubes 26 to 32), two pump chambers P1 and P2, nine interior liquid paths F1 to F9, and ten valve stations V1 to V10.

The two pump chambers P1 and P2 are formed as wells that open on the front side 58 of the cassette 24. Upstanding edges 62 peripherally surround the open wells of the pump chambers P1 and P2 on the front side 58 of the cassette 24 (see FIG. 6B).

The wells forming the pump chambers P1 and P2 are closed on the back side 60 of the cassette 24 (see FIG. 6), except that each pump chamber P1 and P2 includes a vertically spaced pair of through holes or ports 64/66 that extend through to the back side 60 of the cassette 24.

As FIGS. 6, 6A and 6B show, vertically spaced ports 64(1) and 66(1) are associated with pump chamber P1. Port 64(1) communicates with liquid path F6, while port 66(1) communicates with liquid path F8.

As FIGS. 6, 6A and 6B also show, vertically spaced ports 64(2) and 66(2) are associated with pump chamber P2. Port 64(2) communicates with liquid path F7, while port 66(2) communicates with liquid path F9.

As will become apparent, either port 64(1)/(2) or 66(1)/(2) can serve its associated chamber P1/P2 as an inlet or an outlet.

Alternatively, liquid can be brought into and discharged out of the chamber P1/P2 through the same port associated 64(1)/(2) or 66(1)/(2).

In the illustrated and preferred embodiment, the ports 64/66 are spaced so that, when the cassette 24 is oriented vertically for use, one port 64(1)/(2) is located higher than the other port 66(1)/(2) associated with that pump chamber P1/P2. As will be described in greater detail later, this orientation provides an important air removal function.

The ten valve stations V1 to V10 are likewise formed as wells open on the front side 58 of the cassette 24. FIG. 6C shows a typical valve station $V_N$. As FIG. 6C best shows, upstanding edges 62 peripherally surround the open wells of the valve stations V1 to V10 on the front side 58 of the cassette 24.

As FIG. 6C best shows, the valve stations V1 to V10 are closed on the back side 60 of the cassette 24, except that each valve station $V_N$ includes a pair of through holes or ports 68 and 68'. One port 68 communicates with a selected liquid path $F_N$ on the back side 60 of the cassette 24. The other port 68' communicates with another selected liquid path $F_N$, on the back side 60 of the cassette 24.

In each valve station $V_N$, a raised valve seat 72 surrounds one of the ports 68. As FIG. 6C best shows, the valve seat 72 terminates lower than the surrounding peripheral edges 62. The other port 68' is flush with the front side 58 of the cassette.

As FIG. 6C continues to show best, the flexible diaphragm 59 overlying the front side 58 of the cassette 24 rests against the upstanding peripheral edges 62 surrounding the pump chambers and valve stations. With the application of positive force uniformly against this side 58 of the cassette 24 (as shown by the f-arrows in FIG. 6C), the flexible diaphragm 59 seats against the upstanding edges 62. The positive force forms peripheral seals about the pump chambers P1 and P2 and valve stations V1 to V10. This, in turn, isolates the pump chambers P1 and P2 and valve stations V1 to V10 from each other and the rest of the system. The cycler 14 applies positive force to the front cassette side 58 for this very purpose.

Further localized application of positive and negative fluid pressures upon the regions of the diaphragm 59 overlying these peripherally sealed areas serve to flex the diaphragm regions within these peripherally sealed areas.

These localized applications of positive and negative fluid pressures on the diaphragm regions overlying the pump chambers P1 and P2 serve to move liquid out of and into the chambers P1 and P2.

Likewise, these localized applications of positive and negative fluid pressure on the diaphragm regions overlying the valve stations V1 to V10 will serve to seat and unseat these diaphragm regions against the valve seats 72, thereby closing and opening the associated valve port 68. FIG. 6C shows in solid and phantom lines the flexing of the diaphragm 59 relative to a valve seat 72.

In operation, the cycler 14 applies localized positive and negative fluid pressures to the diaphragm 59 for opening and closing the valve ports.

The liquid paths F1 to F9 are formed as elongated channels that are open on the back side 60 of the cassette 24. Upstanding edges 62 peripherally surround the open channels on the back side 60 of the cassette 24.

The liquid paths F1 to F9 are closed on the front side 58 of the cassette 24, except where the channels cross over valve station ports 68/68' or pump chamber ports 64(1)/(2) and 66(1)/(2).

The flexible diaphragm 61 overlying the back side 60 of the cassette 24 rests against the upstanding peripheral edges 62 surrounding the liquid paths F1 to F9. With the application of positive force uniformly against this side 60 of the cassette 24, the flexible diaphragm 61 seats against the upstanding edges 62. This forms peripheral seals along the liquid paths F1 to F9. In operation, the cycler 14 also applies positive force to the diaphragm 61 for this very purpose.

As FIGS. 6, 6A and 6B show, five premolded tube connectors 27/29/31/33/35 extend out along one side edge of the cassette 24. When the cassette 24 is vertically oriented for use, the tube connectors 27 to 35 are vertically stacked one above the other. The first tube connector 27 is the uppermost connector, and the fifth tube connector 35 is the lowermost connector.

As FIG. 2 shows the cycler 14 carries the operating elements essential for an APD procedure within a portable housing 82. The housing 82 also includes an exterior support plate 94 on the top of the cycler housing 82 for carrying the heater bag 22 (as FIG. 1 shows). The support plate 94 is made of a heat conducting material, like aluminum. Thermocouples T5/T6 (see FIG. 2) independently monitors the temperature of the heater bag 22 itself. In one embodiment, the controller 16 includes a heater control algorithm that elevates the temperature of liquid in the heater bag 22 to about 33 degrees C. before the first fill cycle. A range of other safe temperature settings could be used, which could be selected by the user. The heating continues as the first fill cycle proceeds until the heater bag temperature reaches 36 degrees C.

2. Alternate Dialysis Systems and Methods

Dialysate solution contained in pre-mixed bags (such as those shown as 20 and 22 in FIG. 1) may contain a variety of formulations. Certain of these formulations, while perhaps otherwise desirable, may not be stable or may not be as stable as other less desirable solutions. For example, in some formulations, carbon dioxide can pass through the bag material and the remaining calcium carbonate could then fall out of solution. In instances where the dialysate formulation is not stable or less stable than other solutions, In such instances, when a bag of dialysate solution may have become unstable, valuable information regarding whether the formulation of the dialysate solution has change and/or whether the dialysate solution is safe to use for a PD treatment may be determined based on the conductivity of the solution.

Additionally, in other embodiments, the cycler may receive dialysis from sources other than the pre-mixed bags (shown as 20 and 22 in FIG. 1). For example, the set may be connected to a bag that contains two or more components that are stored separately from each other, such as in a multi-chamber container, until the components are mixed together to form the dialysate. One embodiment of a multi-chamber container is described in U.S. Pat. No. 7,122,210, which is hereby incorporated by reference herein. Such multi-chamber bags allow a variety of different dialysate compositions to be utilized during PD, including solution containing a variety of buffering agents, including bicarbonate. By way of example, in multi-chamber containers of the type described in U.S. Pat. No. 7,122,210, two components are stored in separate, hydraulically connected chambers of a multi-chamber container. The contents of the two chambers are then combined prior to utilization of the dialysate solution by removing what is called a "peel seal" to hydraulically connect the two chambers and mix the two components. However, due to human error or otherwise, the two components may not be properly mixed before a patient attempts to use the dialysate to conduct a PD treatment. In such instances, valuable information regarding whether the formulation of the dialysate solution is appropriate and/or whether the dialysate solution is safe to use for a PD treatment may be determined based on the conductivity of the solution.

In other embodiments, the cycler may be connected to a system for preparing dialysate rather than in bagged dialysate of the types described above. Such systems may prepare all or substantially all of the dialysate necessary for a complete PD treatment in one batch in advance of the PD treatment, may prepare the dialysate in a number of smaller batches before and/or during the PD treatment, or may prepare the dialysate in real time or close to real time during the PD treatment. Again, in such instances, valuable information regarding whether the formulation of the dialysate solution is appropriate and/or whether the dialysate solution is safe to use for a PD treatment may be determined based on the conductivity of the solution.

In further embodiments, a heating system other than the support plate 94 and associated thermocouples described above may be utilized to maintain the temperature of the dialysate at a certain temperature or within a certain temperature range. Alternate heating systems include the use of an in-line heater element. In such instances, determining the temperature of the dialysate solution and comparing that temperature to a known value, which known value may change from time to time during the PD therapy as discussed above, is valuable.

In each of these instances in which one or more properties of the dialysate is determined, it is also valuable to have both an accurate measurement apparatus to measure the temperature, conductivity, and/or other property of the dialysate in the cassette while avoiding contamination between with the measurement apparatus and the dialysate, such that part or all of the sensor apparatus can be reused and need not be disposed of along with the disposable cassette.

3. Cassette with Sensor Apparatus for Peritoneal Dialysis

Figure 7A:
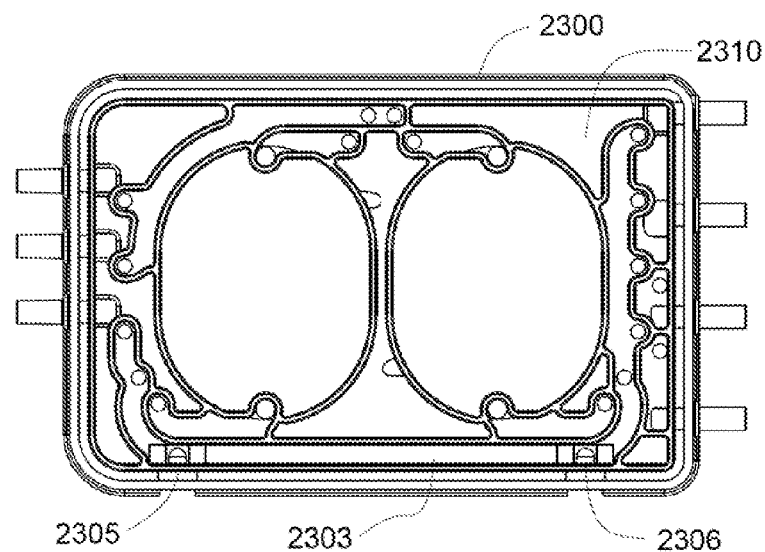
FIG. 7A is a section view of the back side of an exemplary cassette.
Figure 7B:
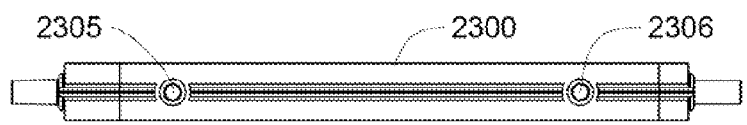
FIG. 7B is a side view of the side of an exemplary cassette.
Figure 7C:
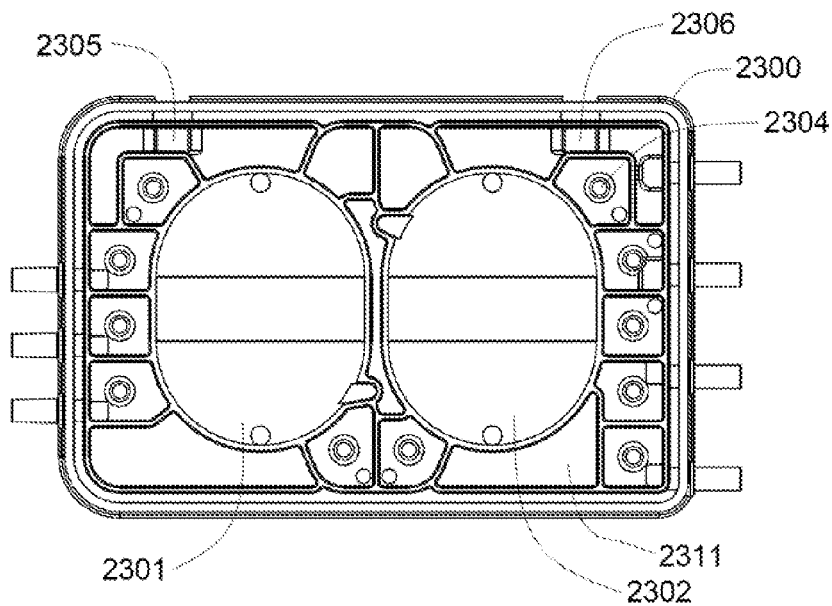
FIG. 7C is a section view of the front of an exemplary cassette.

FIGS. 7A-C show another exemplary embodiment of a flexible membrane cassette of a similar type to those generally described above. FIGS. 7A-C shows back, side, and front views of exemplary cassette 2300. As FIGS. 7A-C show, the cassette 2300 includes an injection molded body having back side 2310 shown in FIG. 7A and front side 2311 shown in FIG. 7C. A flexible diaphragm (one of which is shown as 59 in FIG. 24) overlies the front side and back side of cassette 2300.

The cassette 2300 is preferably made of a rigid plastic material and the diaphragms are preferably made of flexible sheets of plastic, although many other materials may be utilized.

Exemplary cassette 2300 forms an array of interior cavities in the shapes of wells and channels. In exemplary cassette 2300, the interior cavities create multiple paths, such as fluid path 2303, to convey liquid (as FIG. 7A shows). In exemplary cassette 2300, the interior cavities also create pump chambers, such as pump chambers 2301 and 2302 (as FIG. 7C shows) and multiple valve stations, such as valve station 2304 (as FIG. 7C shows). In the exemplary cassette 2300, the valve stations, such as valve station 2304, interconnect the multiple liquid paths, such as fluid path 2303, with pump chambers 2301 and 2302 and with each other.

In certain embodiments, exemplary cassette 2300 may be utilized in conjunction with a device (not shown here, but of the type generally shown in FIG. 1, 14) that locally applies positive and negative pressure, including positive and negative fluid pressure of the type described above and in U.S. Pat. No. 5,350,357, on the diaphragm regions overlying the valve stations and pump chambers. While many different types of pump chambers and valves may be utilized with cassette of the types described herein (or, in certain embodiments, not included at all), exemplary pump chambers and valve stations of the type shown in FIGS. 7A-C are described in more detail above and in U.S. Pat. No. 5,350,357, incorporated herein. The presence, number, and arrangement of the pump chambers, liquid paths, and valve stations can vary. Additionally, alternative or additional cassette functionality may be present in a given cassette.

With further reference to FIGS. 7A-C, exemplary cassette 2300 includes sensor ports 2305 and 2306 that extend into fluid path 2303. Sensor ports 2305 and 2306 may be used to insert a sensing probe, thermal well or other sensing element to allow. Exemplary cassette 2300 shows two sensor ports per cassette, but one port, two ports, or more than two ports may be used depending on the configuration of the cassette and the type of sensor or sensors used.

Again, with reference to FIG. 7A-C, exemplary cassette 2300 is shown with sensor ports 2305 and 2306 position in the rigid body of cassette 2300. In the case of a rigid cassette body with two flexible membranes, one on either side of the rigid body, as shown in FIG. 7A-C, in one embodiment sensor ports 2305 and 2306 may be position in the rigid body portion of the cassette (as shown best in FIG. 7B). However, in other embodiments, the sensor port may extend though one or more areas of the flexible diaphragm overlying the cassette.

Figure 8:
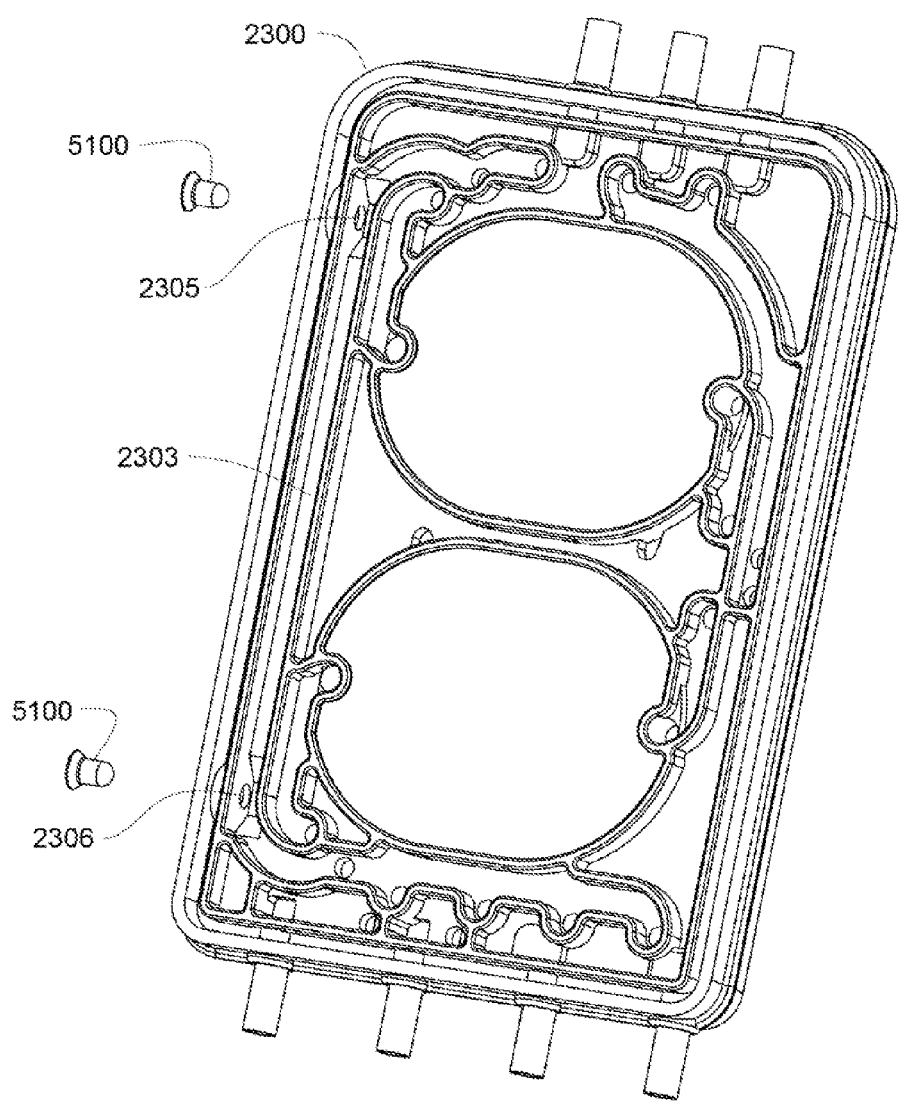
FIG. 8 is a view of an exemplary cassette and thermal wells.

Referring now to FIG. 8, exemplary cassette 2300 is shown with sensor ports 2305 and 2306 extending into fluid path 2303 such that a component placed in sensor ports 2305 and 2306 would come into direct contact with the dialysate contained in or flowing through fluid path 2303. FIG. 8 additionally shows thermal wells 5100 positioned near sensor ports 2305 and 2306. In this embodiment, cassette 2300 and thermal wells 51.00 are separate parts. In some embodiments, the cassette 2300 and the thermal well 5100 are made from different materials. For these embodiments, the thermal well 5100 can be made from any materials, including but not limited to, plastic, metal, ceramic or a combination thereof. The material may depend in some part on the compatibility with the intended dialysate formulation. In other embodiments, thermal well 5100 could be made from the same material as cassette 2300. In yet further embodiments, thermal well 5100 could be formed as a part of the structure of the rigid body of cassette 2300.

The length and width of the thermal well 5100 utilized with exemplary cassette 2300 can be any length and width having the desired or tolerable accuracy characteristics and which properly positions any sensor or sensing probe utilized with thermal well 5100 sufficiently in contact with the dialysate contained in or flowing through fluid path 2306. The length of thermal well 5100 may impact the fluid flow of the dialysate in fluid path 2303 to a certain extent. It also should be understood that the length of the thermal well 5100 may also impact the turbulence of the fluid flow. Thus, the length and width of the thermal well 5100 may be changed to have greater or lesser impact on the fluid flow and turbulence of the fluid, while mitigating the other variables.

The shape of the thermal well 5100 is also a variable. Any shape desired is contemplated. However, the shape of the thermal well 5100, as with the other variables, is determined in part based on the intended use of the sensor apparatus. For purposes of description, an exemplary embodiment is described herein. However, the shape in the exemplary embodiment is not meant to be limiting. All of the various embodiments of thermal wells described herein may be used in conjunction with cassettes, such as exemplary cassette 2300.

Figure 9:
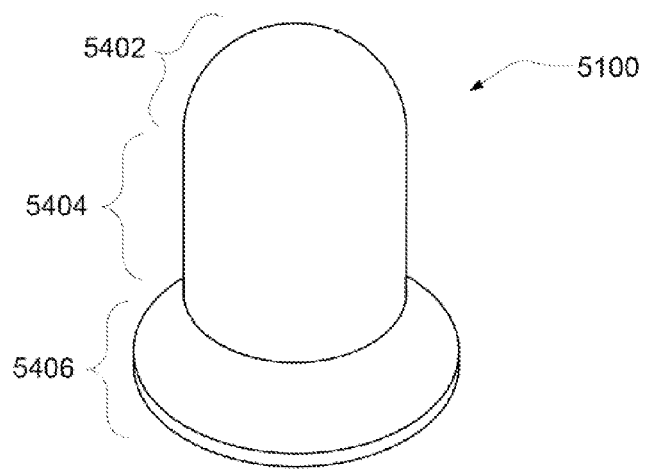
FIG. 9 is a pictorial view of a thermal well according to one embodiment of the sensing apparatus.

Referring now FIG. 9 for purposes of description, the thermal well 5100 has been divided into three zones. The top zone 5402 communicates with the sensing probe (not shown); the middle zone 5404 provides the desired length of the thermal well 5100. As described above, the length may dictate the level of protrusion into the fluid path. The length is dictated in part by the desired performance characteristics as discussed above. The middle zone 5404 also isolates the top zone 5402 from the ambient. The middle zone 5404 may also serve to locate, fasten or seal the thermal well 5100 into the cassette.

The bottom zone 5406, which in some embodiments may not be necessary (see FIG. 19K) thus, in these embodiments, the middle zone 5404 and the bottom zone 5406 may be a single zone. However, in the exemplary embodiment, the bottom zone 5406 is shaped to aid in press fitting the thermal well into an area in the fluid line and may locate and/or fasten the thermal well 5100 into the fluid line 5108. In other embodiments, zone 5406 may be formed to facilitate various joining methods (see FIGS. 19A-19J, 19L-19S)

Figure 10:
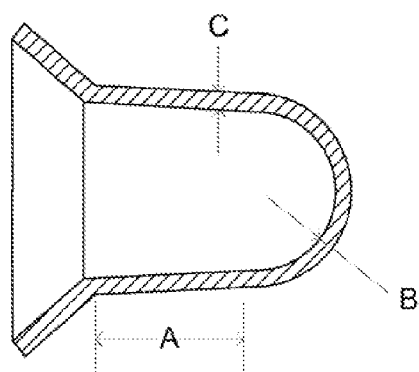
FIG. 10 is a cross sectional view of an exemplary embodiment of the thermal well.

Referring now to FIG. 10 a cross section of the exemplary embodiment of the thermal well 5100 is shown. The dimensions of the exemplary embodiment of the thermal well 5100 include a length A of approximately 0.113 inches (with a range from 0-0.379 inches), a radius B of approximately 0.066 inches and a wall thickness C ranging from approximately 0.003-0.009 inches. These dimensions are given for purposes of an exemplary embodiment only. Depending on the variables and the intended use of the sensing apparatus, the thermal well 5100 dimensions may vary, and the various embodiments are not necessarily proportional.

In some embodiments, the wall thickness can be variable, i.e., the wall thickness varies in different locations of the thermal well. Although these embodiments are shown with variable thicknesses in various locations, this is for description purposes only. Various embodiments of the thermal well may incorporate varying wall thickness in response to variables, these varying wall thicknesses can be "mixed and matched" depending on the desired properties of the sensing apparatus. Thus, for example, in some embodiments, a thinner zone 5404 may be used with thinner zone 5406 and vice-versa. Or, any other combination of "thinner" and "thicker" may be used. Also, the terms used to describe the wall thicknesses are relative. Any thickness desired is contemplated. The figures shown are therefore for descriptive purposes and represent two embodiments where many more are contemplated.

Figure 11A:
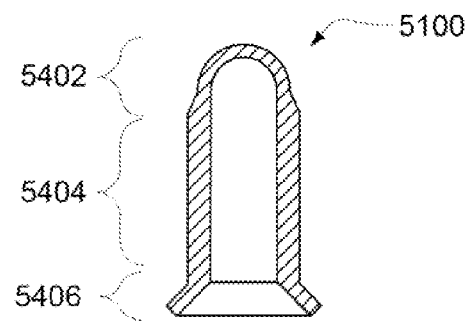
FIGS. 11A and 11B show section views of embodiments of thermal wells having variable wall thickness.
Figure 11B:
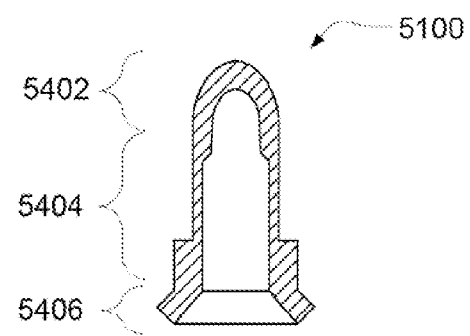

Referring now to FIGS. 11A and 11B, zone 5402 can be thicker or thinner as desired. The thinner zone 5402, amongst other variables, generally provides for a faster sensing time while a thicker zone may be useful for harsh environments or where sensor damping is desired. Zone 5404 may be thicker, amongst other variables, for greater strength or thinner for, amongst other variables, greater isolation from ambient. Zone 5406 can be thinner or thicker depending on the fastening method used.

Figure 12:
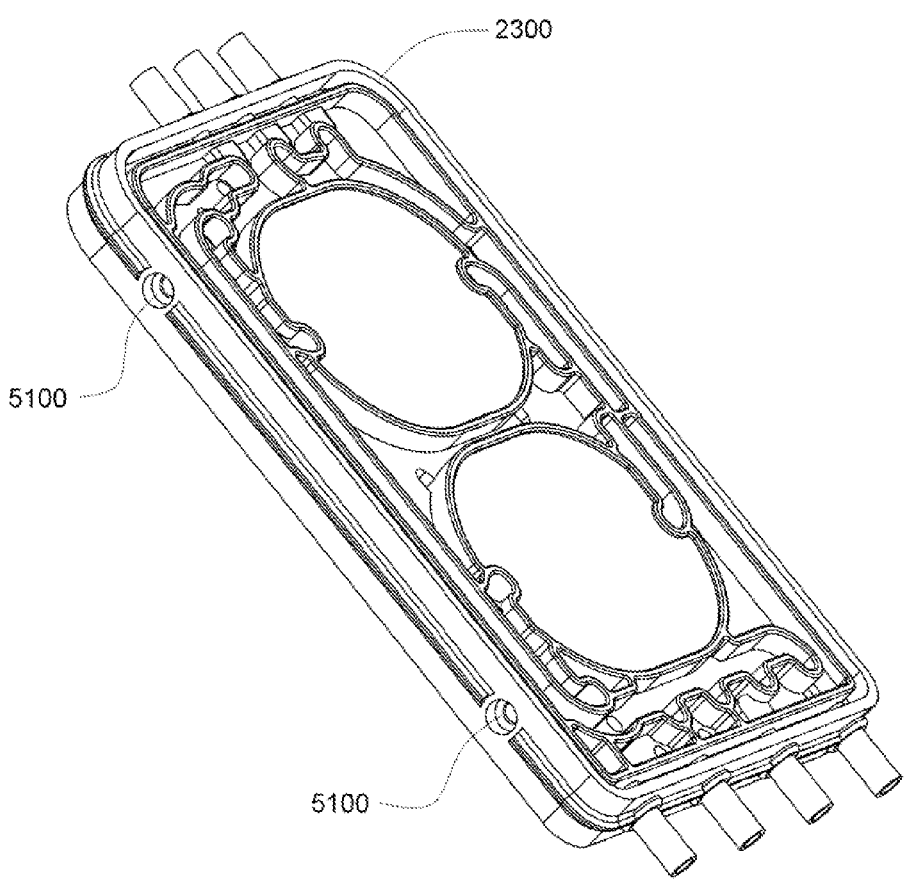
FIG. 12 is a view of an exemplary cassette with thermal wells installed.

FIG. 12 shows thermal wells 5100 installed in exemplary cassette 2300. Thermal well 5100 may be installed in exemplary cassette 2300 by use of the ways described herein, including adhesive, welding (ultrasonic and otherwise), o-ring, retaining plate, and otherwise. The thermal well 5100 used in connection with a cassette may be of various shapes and configurations. However, referring now to FIG. 9 for purposes of description, the embodiment of a thermal well 5100 shown may be utilized in conjunction with a cassette. In the exemplary embodiment shown in FIG. 9, the bottom zone 5406 is shaped to aid in press fitting the thermal well into the sensor port 2305 shown in FIGS. 7A-C and 8.

Figure 13:
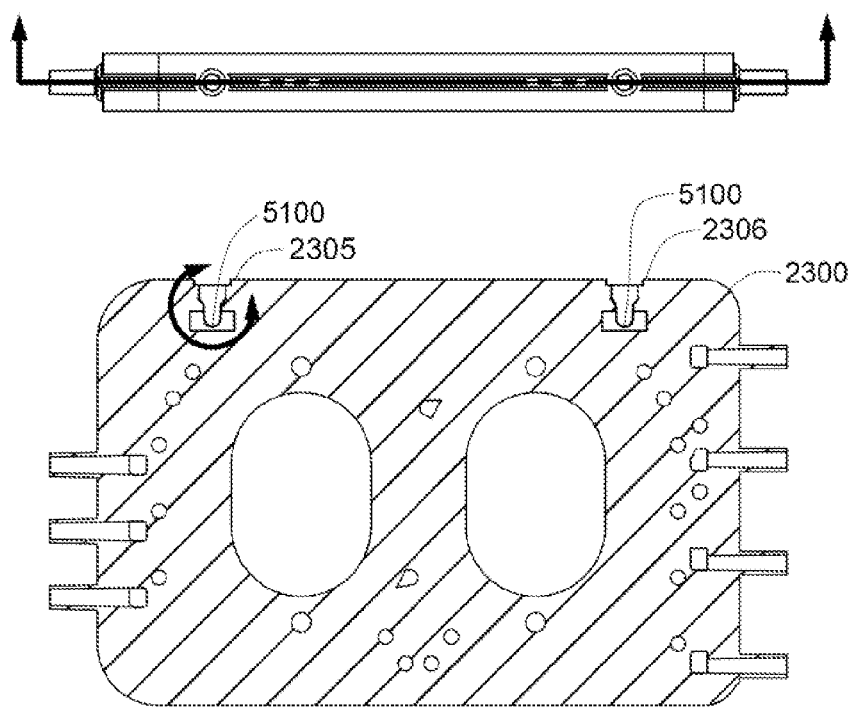
FIG. 13 is a view of the thermal wells extending into a fluid line of an exemplar cassette.

FIG. 13 further shows thermal well 5100 installed in sensor port 2305 and 2306. As may be best shown by FIG. 14, thermal well 5100 extends into fluid path 2303 so that thermal well 5100 may come into direct contact with any dialysate contained in or flowing through exemplary cassette 2300.

In certain embodiments of sensor apparatus and sensor apparatus systems used in conjunction with a flexible membrane cassette, a sensing probe may be installed directly into sensing ports 2305 and 2306 (sensing ports 2305 and 2306 as shown in FIGS. 7A-C and 24). In further embodiments of sensor apparatus and sensor apparatus systems used in conjunction with a flexible membrane, a sensing probe may be used with a thermal well.

Figure 14:
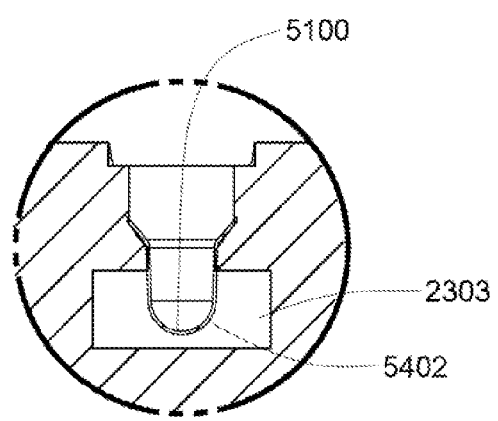
FIG. 14 is a close up certain features of FIG. 13.

As can be seen in FIG. 14, dialysate is in contact with the outside of zone 5402 of the thermal well 5100. Thermal energy is transferred from the dialysate to the thermal well 5100. As may be seen with reference to FIG. 13A-B, the thermal energy can them be further transferred to the tip 6002 of the sensing probe 6000. Thermal energy is then conducted to the thermal sensor 6014. The thermal sensor 6014 communicates via leads 6016 with equipment that can determine the temperature of the dialysate based on feedback of the thermal sensor 6014. In embodiments where conductivity sensing is also desired, lead 6018 communicates with equipment that can determine the conductivity of the dialysate. With respect to determining the conductivity of the dialysate, in addition to the lead 6018, a second electrical lead/contact (not shown) would also be used. The second lead could be any probe or apparatus capable of sensing capacitance of the dialysate, including, an electrical contact.

Heat transfer from the tip 6002 to the thermal sensor 6014 may be improved by the use of a thermal epoxy or thermal grease 6022.

Many different embodiments of sensing apparatus may be used in connection with a thermal well installed in a flexible cassette, including embodiments similar to those described below. While several geometries have been described, many others could be shown to achieve desired performance characteristics.

In certain embodiments, exemplary cassette 2300 may be utilized in conjunction with a device (an exemplary cycler is shown in FIG. 1, 14) that locally applies positive and negative pressure, including positive and negative fluid pressure of the type described above and in U.S. Pat. No. 5,350,357, on the diaphragm regions overlying the valve stations and pump chambers. When cassette 2300 is utilized in conjunction with a pressure applying device (not shown), cassette 2300 may be connected to the device in a number of different ways and in a number of different positions.

Preferably, in certain embodiments, cassette 2300 may be loaded in a device in other than a horizontal orientation, such as a vertical or substantially vertical orientation. Placement of the cassette in a vertical or substantially vertical orientation may offer certain advantages depending on the configuration of the cassette such as to avoid air entrapment and to optimize application of positive and negative pressure, including positive and negative fluid pressure of the types described above and in U.S. Pat. No. 5,350,357, to the cassette. In certain embodiments, non-pneumatic pressure may be applied to the cassette to cause pumping, valving, and/or other functions.

Figure 16:
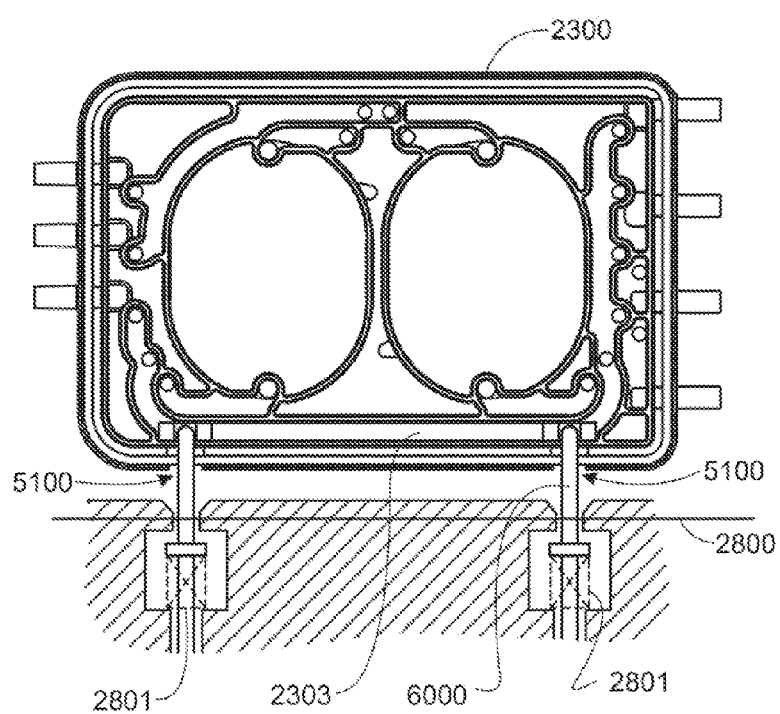
FIG. 16 is a section view showing an embodiment of the cassette engaged with a housing and illustrating engagement of sensing probes located in the housing with sensor ports of the cassette.

Referring now to FIG. 16, a sensor apparatus system of the type generally shown may be used in connection with exemplary cassette 2300. In the system, the sensor apparatus is installed in sensor ports 2305 and 2306 (not shown) extending into fluid path 2303. The sensor apparatus includes the sensing probe 6000 and the thermal well 5100. In this embodiment, the thermal well 5100 and fluid line 2303 is contained in an exemplary cassette 2300. In certain embodiments, exemplary cassette 2300 is intended to be disposable. Sensing probe 6000 is mounted in a reusable portion. Also in the reusable portion is a spring 2801. The spring 2801 and sensing probe 6000 are located in a housing 2800. The housing 2800 can be in any machine, container, device or otherwise. In certain embodiments the reusable portion in contained in or otherwise a part of a pressure applying device (such as shown in FIG. 1, 14). The spring 2801 can be a conical, a coil spring, wave spring, or urethane spring. Alternatively, any other apparatus for biasing the sensing probe to ensure an appropriate fit in thermal well 5100 may be used, including the apparatus described below.

In certain embodiments, the thermal well 5100 and the sensing probe 6000 may include alignment features (of the type shown in FIG. 32, 6702, 6704) that aid in the thermal well 5100 and sensing probe 6000 being aligned. The correct orientation of the thermal well 5100 and the sensing probe 6000 may aid in the mating of the thermal well 5100 and the sensing probe 6000 to occur. Referring again to FIG. 216, the configuration of the housing 2800 may provide the sensing probe 6000 with space for lateral movement. This allows the sensing probe 6000 to, if necessary; move laterally in order to align with the thermal well 5100 for mating.

In various embodiments, the sensing probe 6000 is configured with respect to the housing 2800 (as shown in FIG. 16) to facilitate engagement between the sensing probe 6000 and the thermal well 5100 and to aid in establishing full contact of the sensing probe 6000 and the thermal well 5100. Variations of the configurations generally shown in FIGS. 33-35 and described above may be used in conjunction with exemplary cassette 2300.

In other embodiments, the sensing probe may be aligned and positioned by other housing configurations. Thus, the embodiments of the housing shown herein are only some embodiments of housings in which the sensor apparatus can be used. The sensor apparatus generally depends on being located amply with respect to the dialysate. The configurations that accomplish this can vary depending on the dialysate and the intended use of the sensing apparatus. Further, in some embodiments where the thermal well is not used, but rather, the sensing probe is used only. The housing configurations may vary as well.

Figure 28:
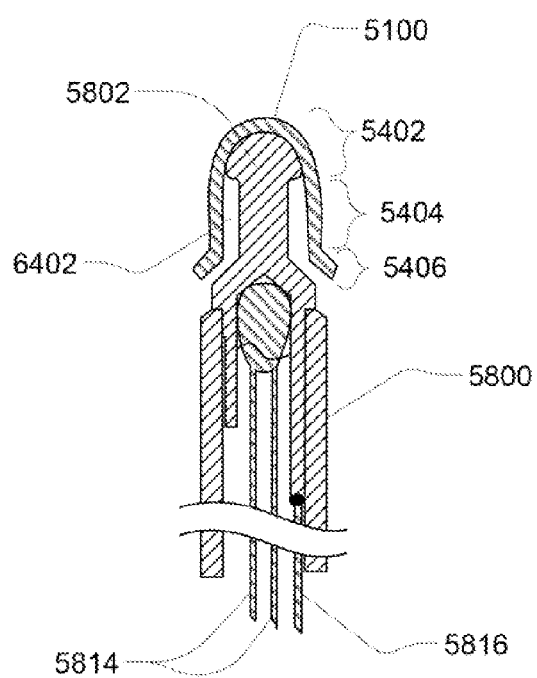
FIG. 28 is a section view of a sensing probe coupled to a thermal well.

In embodiments in which cassette 2300 is loaded into a device, such as a pressure applying device or a cycler (as shown in FIG. 1, 14), particularly when cassette 2300 is loaded into the device or cycler in a vertical or substantially vertical orientation, it may be preferable for sensor ports 2305 and 2306 to be positioned in the bottom edge of cassette 2300 (the bottom edge as the cassette is shown in FIG. 7A). Positioning of the sensor ports 2305 and 2306 along the bottom edge of exemplary cassette 2300 (such that sensor ports 2305 and 2306 and installed thermal wells 5100 extend into the bottom fluid line 2303 of the cassette) may facilitate engagement with the sensor apparatus as shown in FIG. 28. In certain of these embodiments, the exemplary cassette 2300 with installed thermal wells 51.00 may be placed in position over sensor probes 6000, and then rotated vertically down and onto the sensor probes 6000.

The sensing apparatus, in some embodiments, is used to sense conductivity of the dialysate within a fluid line within a cassette. In some embodiments, this is in addition to temperature sensing. In those embodiments where both temperature and conductivity sensing is desired, the sensing probe typically includes at least three leads, where two of these leads may be used for temperature sensing and the third used for conductivity sensing.

Figure 15:
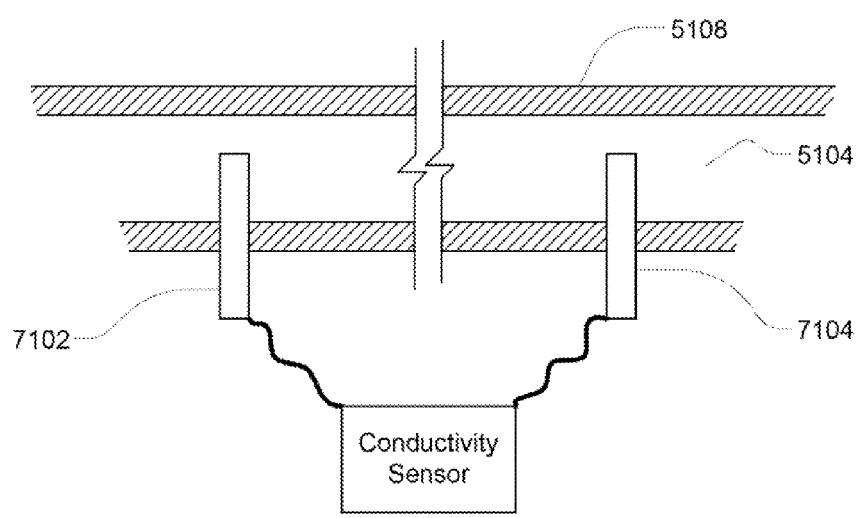
FIG. 15 is a section view of one embodiment of a sensing probe coupled to a thermal well installed in a cassette and suspended by a spring.

Referring now to FIG. 15, for conductivity sensing, at least two sensors 7102, 7104 are located in an area containing the dialysate. In the embodiment shown, the area containing the dialysate is a fluid path 5104 inside a fluid line 5108. The conductivity sensors 7102, 7104 can be one of the various embodiments of sensing probes as described above, or one of the embodiments of the sensor apparatus embodiments (including the thermal well) as described above.

Referring now to FIG. 16, sensing probes 6000 installed in thermal wells 5100 in sensor ports 2305 and 2306 can be used for sensing the conductivity of the dialysate located between sensor ports 2305 and 2306 in fluid line 2303. However, in other embodiments, only one of the sensors is one of the embodiments of the sensor apparatus or one of the embodiments of the sensing probe, and the second sensor is any electrical sensor known in the art. Thus, in the systems described herein, conductivity and temperature can be sensed through using either one of the sensor apparatus or one of the sensor probes as described herein and a second capacitance sensor, or one of the sensor apparatus or one of the sensor probes as described herein and an electrical sensor.

Temperature sensing may be used as a part of various safety apparatus and procedures. Temperature sensing may be used to measure the temperature of the dialysate in the cassette before the dialysate enters the patient's peritoneum. Alternatively, temperature sensing may be used to measure the temperature of the dialysate in the cassette before the dialysate enters the patient's peritoneum. In other embodiments, temperature sensing may be used to measure the temperature of the dialysate in the cassette before and after the dialysate enters the patient's peritoneum. Temperature measurements may be sent to cycler (shown in FIG. 1, 14) and/or the controller (shown in FIG. 1, 16). Temperature measurements may be taken at predetermined times, regular, intervals, or on demand. Temperature measurements may be displayed to the patient. In other embodiments, the temperature measurements are compared against a desired value or against a desired range. In certain embodiments, the cycler (shown in FIG. 1, 14) and/or the controller (shown in FIG. 1, 16) may cause a notice or alarm to be displayed to the patient indicating that the temperature is outside of certain parameters. In other embodiments, the cycler (shown in FIG. 1, 14) and/or the controller (shown in FIG. 1, 16) may not start a PD treatment if the temperature is outside of certain parameters. In other embodiments, the cycler (shown in FIG. 1, 14) and/or the controller (shown in FIG. 1, 16) may stop or delay a PD treatment if the temperature is outside of certain parameters. In various embodiments, the temperature of the dialysate may be measured in one fluid path in the cassette. In other embodiments, the temperature of the dialysate may be measured in multiple fluid paths in the cassette or in all fluid paths in the cassette.

Conductivity sensing may be used (alone or preferably in conjunction with temperature sensing) as a part of various safety apparatus and procedures. Conductivity sensing may be used to measure the conductivity of the dialysate in the cassette before the dialysate enters the patient's peritoneum to determine if the dialysate solution has the expected conductivity and thus may be used to determine if the dialysate is of the expected formulation. Conductivity sensing may be used (alone or preferably in conjunction with temperature sensing) to determine if the dialysate in the pre-mixed bag remains stable. In other embodiments, conductivity sensing may be used (alone or preferably in conjunction with temperature sensing) to determine if the patient or caregiver has appropriately removed the seal and mixed the multiple components in a multi-chamber bag. In other embodiments, conductivity sensing may be used (alone or preferably in conjunction with temperature sensing) to determine if the dialysate prepared in a dialysate preparation system is of the expected conductivity and thus is of the expected formulation, pH, and the like.

In certain embodiments, the cycler (shown in FIG. 1, 14) and/or the controller (shown in FIG. 1, 16) may cause a notice or alarm to be displayed to the patient indicating that the conductivity of the dialysate (or indicating that the dialysate may not be safe for PD treatment based on the conductivity of the dialysate) is outside of certain parameters. In other embodiments, the cycler (shown in FIG. 1, 14) and/or the controller (shown in FIG. 1, 16) may not start a PD treatment if the conductivity of the dialysate is outside of certain parameters. In other embodiments, the cycler (shown in FIG. 1, 14) and/or the controller (shown in FIG. 1, 16) may stop or delay a PD treatment if the conductivity of the dialysate is outside of certain parameters. In various embodiments, the conductivity of the dialysate may be measured in one fluid path in the cassette. In other embodiments, the conductivity of the dialysate may be measured in multiple fluid paths in the cassette or in all fluid paths in the cassette.

4. Alternate Thermal Well Embodiments

Alternate embodiments of thermal wells are described, often in relation to a fluid line. In most embodiments, the fluid line could be the fluid path of a cassette, such as fluid path 2303 of exemplary cassette 2300, described above. Alternatively, the principles described below could also be applicable to any of the cassette embodiment described herein.

In one exemplary embodiment, a thermal well is used to accommodate a sensor probe, such as a temperature sensing probe. The thermal well comes into direct contact with a dialysate and the sensing probe does not. Based on heat transfer dictated in large part by the thermodynamic properties of the thermal well and sensing probe construction, the sensing probe can determine the properties of the dialysate without coming into direct contact with the dialysate. The accuracy and efficiency of the sensor apparatus arrangement depends on many factors including, but not limited to: construction, material and geometry of both the probe and the thermal well.

Figure 16A:
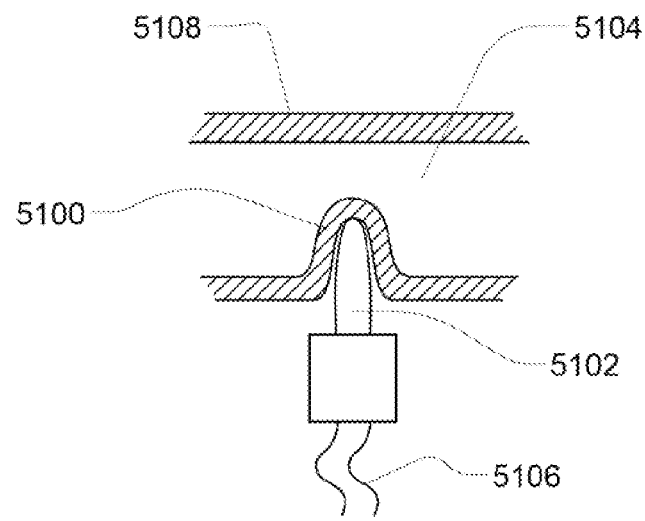
FIGS. 16A and 16B are embodiments of the sensing apparatus where the thermal well is a continuous part of the fluid line.
Figure 16B:
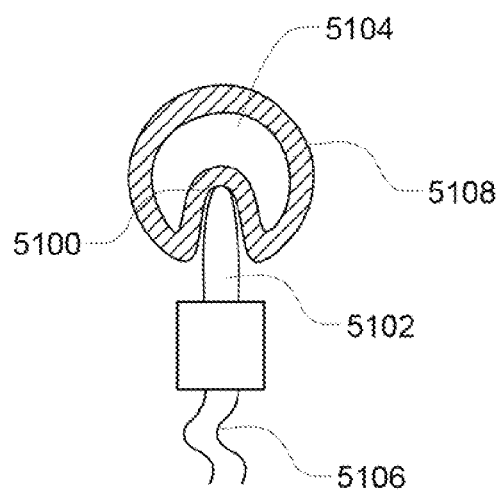

Referring now to FIGS. 16A and 16B, two embodiments of the sensor apparatus which includes the thermal well 5100 and the sensing probe 5102, are shown in relation to a fluid line 5108. In these embodiments, the thermal well 5100 is integrated into the fluid line 5108. However, in other embodiment, some described below, the thermal well 5100 is not completely integrated into the fluid line 5108, i.e., the thermal well 5100 can be made from different materials as compared with the fluid line 5108. In alternate embodiments, the thermal well 5100 is not integrated into any fluid line but can be integrated into anything or nothing at all. For example, in some embodiments, the thermal well 5100 can be integrated into a container, chamber, machine, protective sleeve, fluid pump, pump cassette, disposable unit, manifold, or other assembly, sub-assembly, or component. For purposes of the description, an exemplary embodiment is described for illustrative purposes. The exemplary embodiment includes the embodiment where the thermal well 5100 is in a fluid line. However, the sensor apparatus and the thermal well can be used outside of a fluid line.

Referring now to FIG. 16A, a side view showing a thermal well 5100 formed in a fluid line 5108 which provides the space 5104 for dialysate to flow through, and a sensing probe 5102 is shown. Data from the sensing probe is transmitted using at least one lead 5106. An end view of FIG. 16A is shown in FIG. 16B.

In this embodiment, the thermal well 5100 is one piece with the fluid line 5108. The total area of the thermal well 5100 can vary. By varying the geometry of the thermal well 5100, the variables, including, but not limited to, the thermal conductivity characteristic of the thermal well 5100 and thus, the heat transfer between the thermal well 5100 and the sensing probe 5102 will vary. As described in more detail below, the material construction of the thermal well 5100 is another variable in the sensor apparatus.

In some embodiments, the fluid line 5108 is made from a material having a desired thermal conductivity. This material may vary depending on the purpose. The material can be anything including, but not limited to, any plastic, ceramic, metals or alloys of metals or combinations thereof.

Figure 17A:
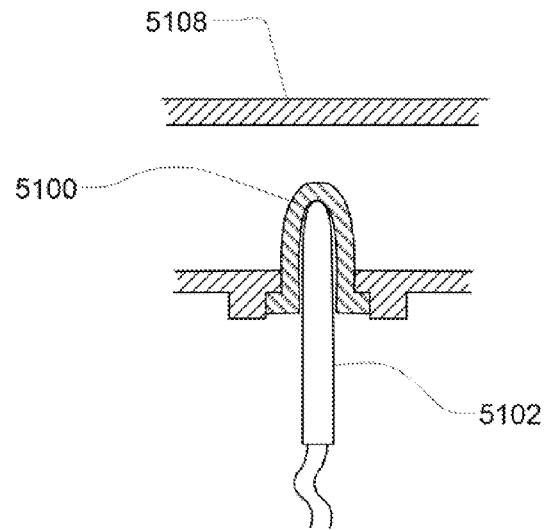
FIGS. 17A and 17B are embodiments of the sensing apparatus where the thermal well is a separate part from the fluid line.
Figure 17B:
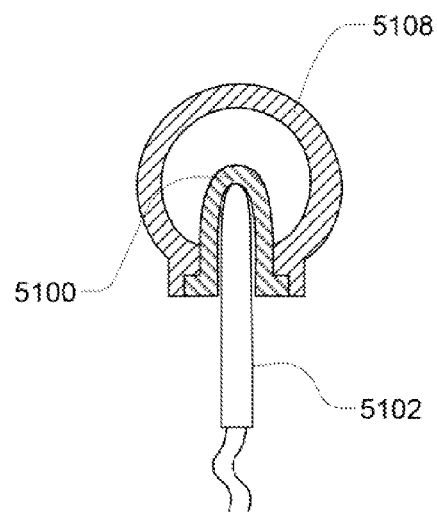

Referring now to FIGS. 17A and 17B, in these embodiments, the fluid line 5108 and the thermal well 5100 are separate parts. In some embodiments, the fluid line 5108 and the thermal well 5100 are made from different materials.

FIGS. 16A-16B and FIGS. 17A-17B show relatively simple embodiments of the sensor apparatus. Thus, for these embodiments, the sensing apparatus includes a thermal well 5100 and a sensing probe 5102 where the thermal well either is integrated as one continuous part with the fluid line 5108 or is a separate part from the fluid line 5108. However, many embodiments of the sensor apparatus are contemplated. Much of the various embodiments include variations on the materials and the geometries of the thermal well 5100 and/or the sensing probe 5102. These variations are dictated by multiple variables related to the intended use for the sensor apparatus. Thus, the dialysate and the constraints of the desired sensor, for example, the accuracy, time for results and the fluid flow and dialysate characteristics are but a sampling of the various constraints that dictate the embodiment used. In most instances, each of the variables will affect at least one part of the embodiment of the sensor apparatus.

Thus, multiple variables affect the various embodiments of the sensor apparatus, these variables include but are not limited to: 1) geometry of the thermal well; 2) material composition of the thermal well; 3) material composition of the sensing probe; 4) desired flow rate of the dialysate; 5) length and width of the thermal well; 6) desired accuracy of the sensing probe; 7) wall thicknesses; 8) length and width of the sensing probe; 9) cost of manufacture; 10) dialysate composition and characteristics including tolerance for turbulence; 11) geometry of sensing probe; and 12) desired speed of readings.

In the foregoing, various embodiments of the sensor apparatus are described. The description is intended to provide information on the affect the variables have on the sensor apparatus embodiment design. However, these are but exemplary embodiments. Many additional embodiments are contemplated and can be easily designed based on the intended use of the sensor apparatus. Thus, by changing one or more of the above mentioned partial list of variables, the embodiment of the sensor apparatus may vary.

Figure 18A:
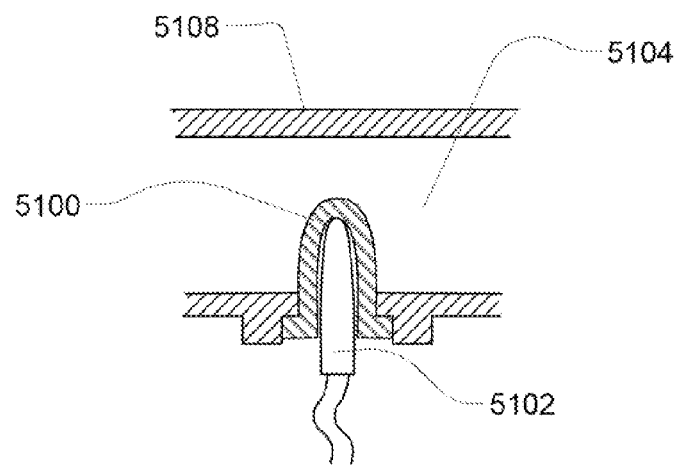
FIGS. 18A and 18B are embodiments of the sensing apparatus showing various lengths and widths of the thermal well.
Figure 18B:
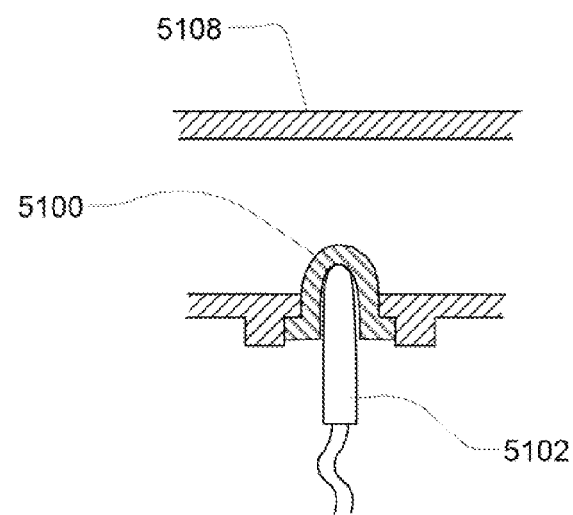

Referring now to FIGS. 18A and 18B, two embodiments of the thermal well 5100 are shown as different parts from the fluid line 5108. These embodiments show two geometries of the thermal well 5100. In FIG. 18A, the geometry includes a longer thermal well 5100. In FIG. 18B, the thermal well 5100 geometry is shorter. The length and width of the thermal well 5100 produce varying properties and accuracies of the thermal conductivity between the thermal well 5100 and the sensing probe 5102. Depending on the use of the sensor apparatus, the thermal well 5100 geometry is one variable.

Referring now to FIG. 18A the longer thermal well 5100 generally provides a greater isolation between the dialysate temperature in the fluid line 5104 and the ambient temperature. Although the longer thermal well 5100 geometry shown in FIG. 18A may be more accurate, the embodiment shown in FIG. 18B may be accurate enough for the purpose at hand. Thus, the length and width of the thermal well 5100 can be any length and width having the desired or tolerable accuracy characteristics. It should be understood that two extremes of length are shown in these embodiments; however, any length is contemplated. The description herein is meant to explain some of the effects of the variables.

Still referring to FIGS. 18A and 18B, the longer thermal well 5100 shown in FIG. 3A may impact the fluid flow of the dialysate in the fluid line 5108 to a greater degree than the embodiment shown in FIG. 18B. It should be understood that the length of the thermal well 5100 may also impact the turbulence of the fluid flow. Thus, the length and width of the thermal well 5100 may be changed to have greater or lesser impact on the fluid flow and turbulence of the fluid, while mitigating the other variables.

The shape of the thermal well 5100 is also a variable. Any shape desired is contemplated. However, the shape of the thermal well 5100, as with the other variables, is determined in part based on the intended use of the sensor apparatus. For purposes of description, an exemplary embodiment is described herein. However, the shape in the exemplary embodiment is not meant to be limiting.

Figure 19A:
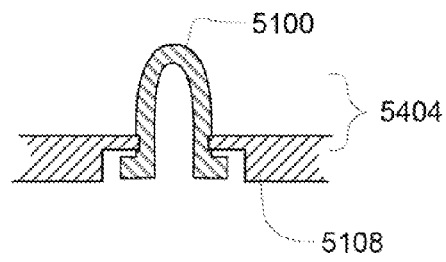
FIGS. 19A-19S are sectional views of various embodiments of the thermal well embedded in a fluid line.
Figure 19B:
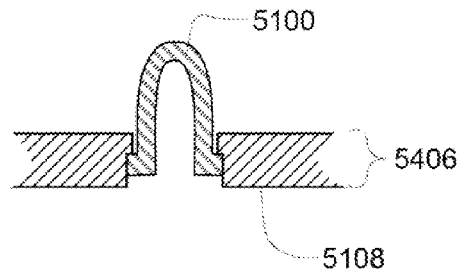
Figure 19C:
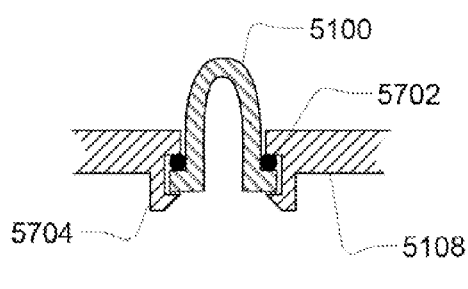
Figure 19D:
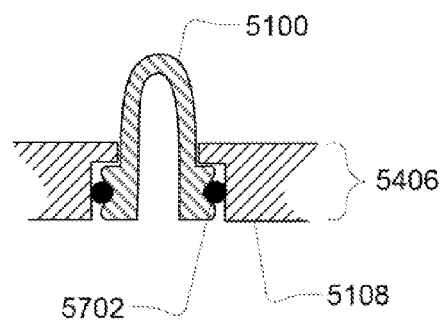
Figure 19E:
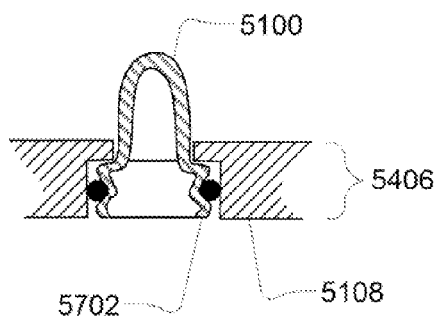

The thermal well 5100, in practice, can be embedded into a fluid line 5108, as a separate part from the fluid line 5108. This is shown and described above with respect to FIGS. 17A-17B. Various embodiments may be used for embedding the thermal well 5100 into the fluid line 5108. Although the preferred embodiments are described here, any method or process for embedding a thermal well 5100 into a fluid line 5108 can be used. Referring now to FIGS. 19A-19S, various configurations for embedding the thermal well 5100 into the fluid line 5108 are shown. For these embodiments, the thermal well 5100 can be made from any materials, including but not limited to, plastic, metal, ceramic or a combination thereof. The material may depend in some part on the compatibility with the intended dialysate. The fluid line 5108, in these embodiments, may be made from plastic, metal, or any other material that is compatible with the dialysate.

Referring first to FIG. 19A, the thermal well 5100 is shown press fit into the fluid line 5108 using the zone 5404 (shown in FIG. 9). In FIG. 19B, the thermal well 5100 is shown press fit into the fluid line 5108 using the zone 5406. Referring now to FIG. 19C, the thermal well 5100 is shown retained in the fluid line 5108 with flexible tabs 5704, an O-ring is also provided. Referring now to FIG. 19D, the thermal well 5100 is shown inserted into the fluid line 5108 with an O-ring 5702. The thermal well 5100 is also shown as an alternate embodiment, where the thermal well 5100 zone 5406 includes an O-ring groove. The O-ring groove can be cut, formed, spun, cast or injection molded into the thermal well, or formed into the thermal well 5100 by any other method. FIG. 19E shows a similar embodiment to that shown in FIG. 19D, however, the O-ring groove is formed in zone 5406 rather than cut, molded or cast as shown in FIG. 19D.

Figure 19F:
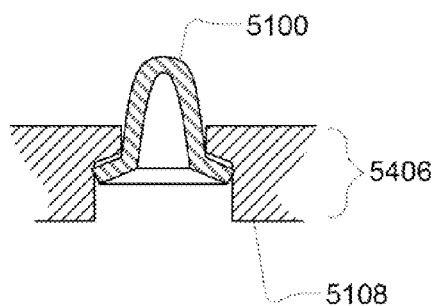
Figure 19G:
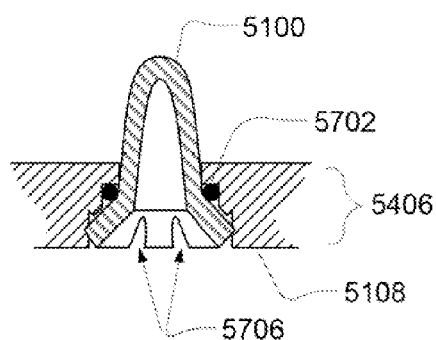

Referring now to FIG. 19F, the thermal well 5100 is shown press fit into the fluid line 5108, zone 5406 includes flexibility allowing the edge of zone 5406 to deform the material of the fluid line 5108. Referring now to FIG. 19G, the thermal well 5100 includes cuts 5706 on the zone 5406 providing flexibility of the zone 5406 for assembly with the fluid line 5108. An O-ring 5702 is also provided. Although two cuts are shown, a greater number or fewer cuts are used in alternate embodiments.

Figure 19H:
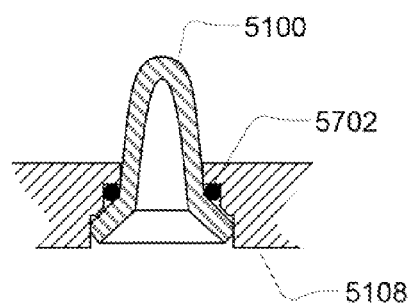
Figure 19I:
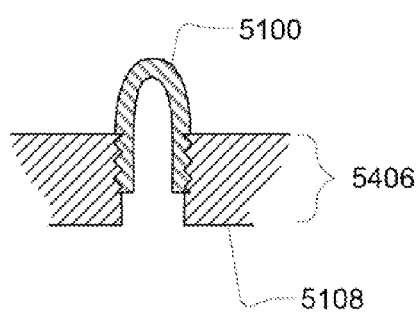

Referring now to FIG. 19H, the embodiment shown in FIG. 19F is shown with the addition of an O-ring 5702. Referring to FIG. 19I, the thermal well 5100 is shown insert molded in the fluid line 5108. Zone 5406 is formed to facilitate or enable assembly by insert molding.

Figure 19J:
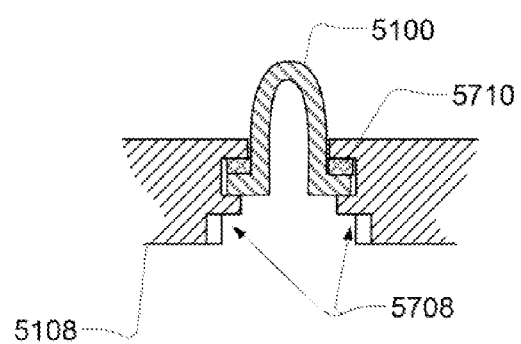

FIG. 19J shows an embodiment where the thermal well 5100 is heat staked 5708 to retain the thermal well 5100 in the fluid line 5108. In some embodiments of FIG. 19J, an O-ring 5710 is also included. In this embodiment, the O-ring 5710 has a rectangular cross section. However, in alternate embodiments, the O-ring may have a round or X-shaped cross section. Likewise, in the various embodiments described herein having an O-ring, the O-ring in those embodiments can have a round, rectangular or X-shaped cross section, or any cross sectional shape desired.

Figure 19K:
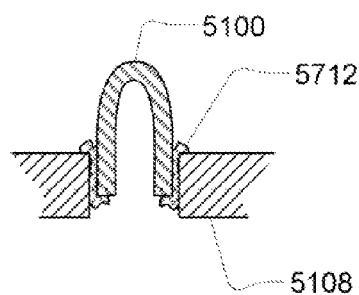

Referring now to FIG. 19K, the thermal well 5100 is retained in the fluid line 5108 by adhesive 5712. The adhesive can be any adhesive, but in one embodiment, the adhesive is a UV curing adhesive. In alternate embodiments, the adhesive may be any adhesive that is compatible with the dialysate. In this embodiment, the thermal well 5100 is shown without a zone 5406.

Figure 19L:
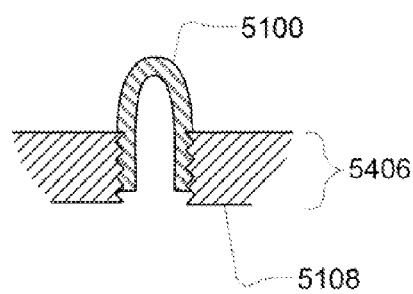

Referring now to FIG. 19L, thermal well 5100 is shown ultrasonically welded in the fluid line 5108. The zone 5406 is fabricated to enable joining by ultrasonic welding.

Figure 19M:
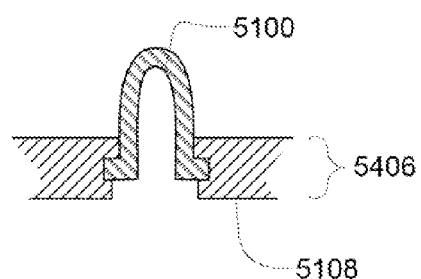

Referring now to FIG. 19M, a thermal well 5100 is shown insert molded in the fluid line 5108. Zone 5406 is a flange for the plastic in the fluid line 5108 to flow around. In the embodiment shown, the flange is flat, however, in other embodiments; the flange may be bell shaped or otherwise.

Figure 19N:
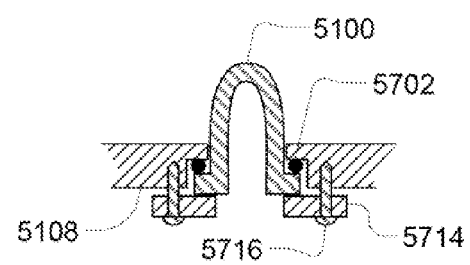

Referring now to FIG. 19N, the thermal well 5100 is shown retained in the fluid line 5108 by a retaining plate 5714 and a fastener 5716. O-ring 5702 is also shown.

Figure 19O:
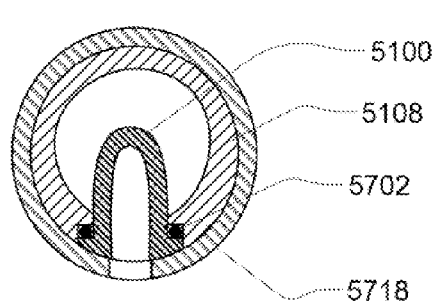
Figure 19P:
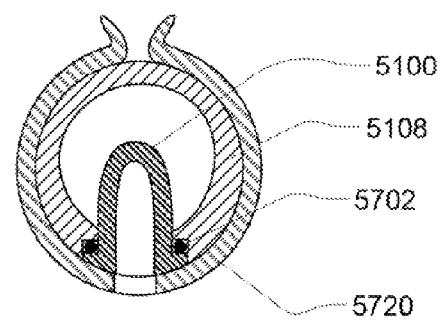

Referring now to FIGS. 19O-19P, an end view is shown of a thermal well 5100 that is retained in a fluid line 5108 by a retaining ring 5718 (FIG. 19O) or in an alternate embodiment, a clip 5720 (FIG. 19P). O-ring 5702 is also shown.

Figure 19Q:
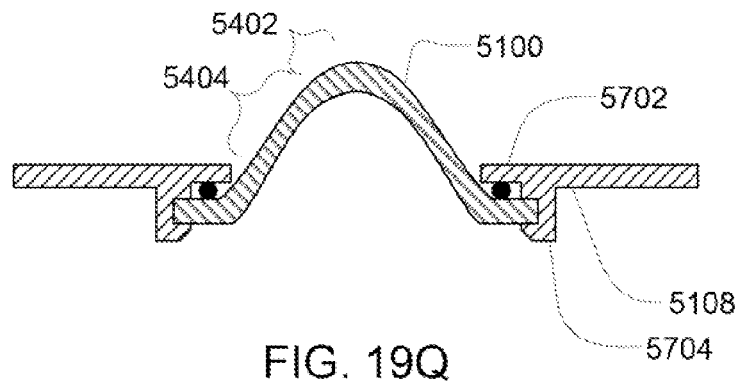

Referring now to FIG. 19Q, the embodiment of FIG. 19C is shown with an alternate embodiment of the thermal well 5100. In this embodiment of the thermal well 5100 the referred to as zone 5404 in FIG. 4 includes a taper that may allow for easier alignment with a sensing probe, better isolation of zone 5402 from the ambient and better flow characteristics in the fluid path. The thermal well 5100 is shown retained in the fluid line 5108 using flexible tabs 5704. An O-ring is also provided.

Figure 19R:
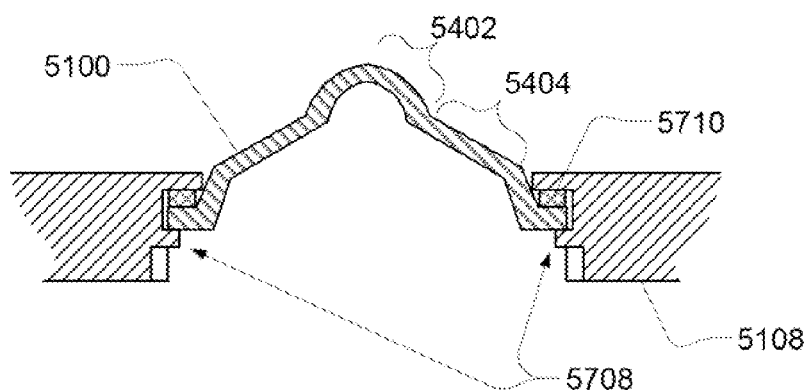
Figure 19S:
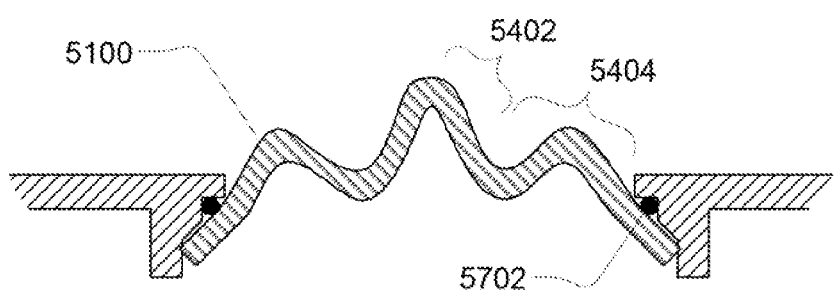

FIG. 19R shows the embodiment of FIG. 19J with an alternate embodiment of the thermal well 5100. The thermal well 5100 shown in this embodiment has a taper in zone 5404 that may allow for easier alignment with a sensing probe, may allow better isolation of zone 5402 from the ambient and may allow better flow characteristics in the fluid path. Zone 5402 provides a hemispherical contact for effective thermal coupling with a thermal probe. The thermal well 5100 is heat staked 5708 to retain the thermal well 5100 in the fluid line 5108. In some embodiments of FIG. 19R, an O-ring 5710 is also included. In this embodiment, the O-ring 5710 has a rectangular cross section. However, in alternate embodiments, the O-ring can have a round or X-shaped cross section.

Referring now to FIG. 19S, the embodiment of FIG. 19H is shown with an alternate embodiment of the thermal well

Figure 4:
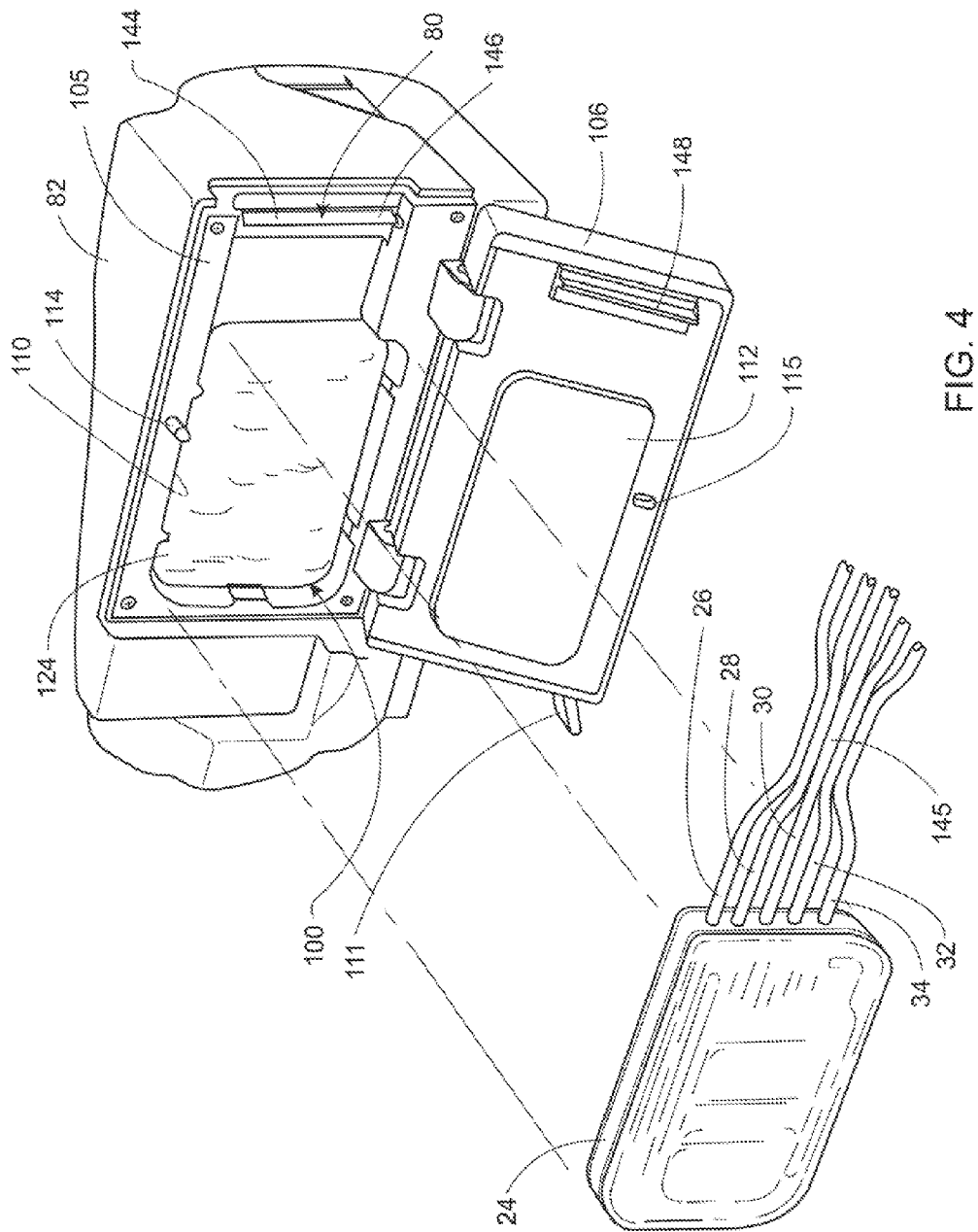
FIGS. 4 and 5 are perspective views of loading the disposable cassette attached to the set shown in FIG. 3 into the cycler for use.
Figure 5:
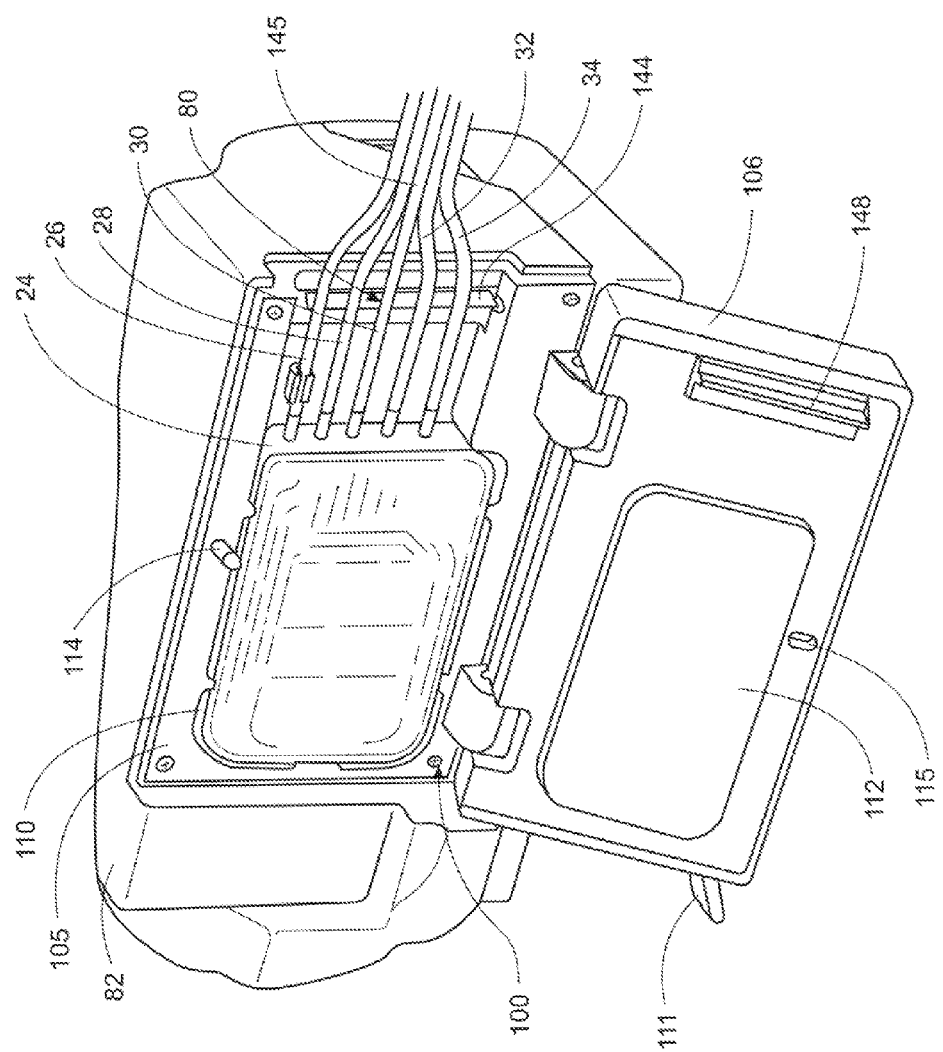

5100. FIG. 19S is shown with the addition of an O-ring 5702. In this embodiment of the thermal well 5100 zone 5404 (as shown in FIG. 4) has convolutions that may allow better isolation of zone 5402 from the ambient. While several geometries have been shown for zone 5404, many others could be shown to achieve desired performance characteristics.

5. Sensing Probe Embodiments

Various embodiments of systems, devices, and methods for sensor interface, including direct sensor contact, sensor interface through the use of a thermal well, or otherwise with various disposable and reusable components are described. Such systems, devices, and methods for sensor interface can be used with a wide variety of sensors and in a wide variety of applications. Such systems, devices, and methods for sensor interface are by no means limited to use with the various sensor embodiments or for use in any particular context.

Figure 20:
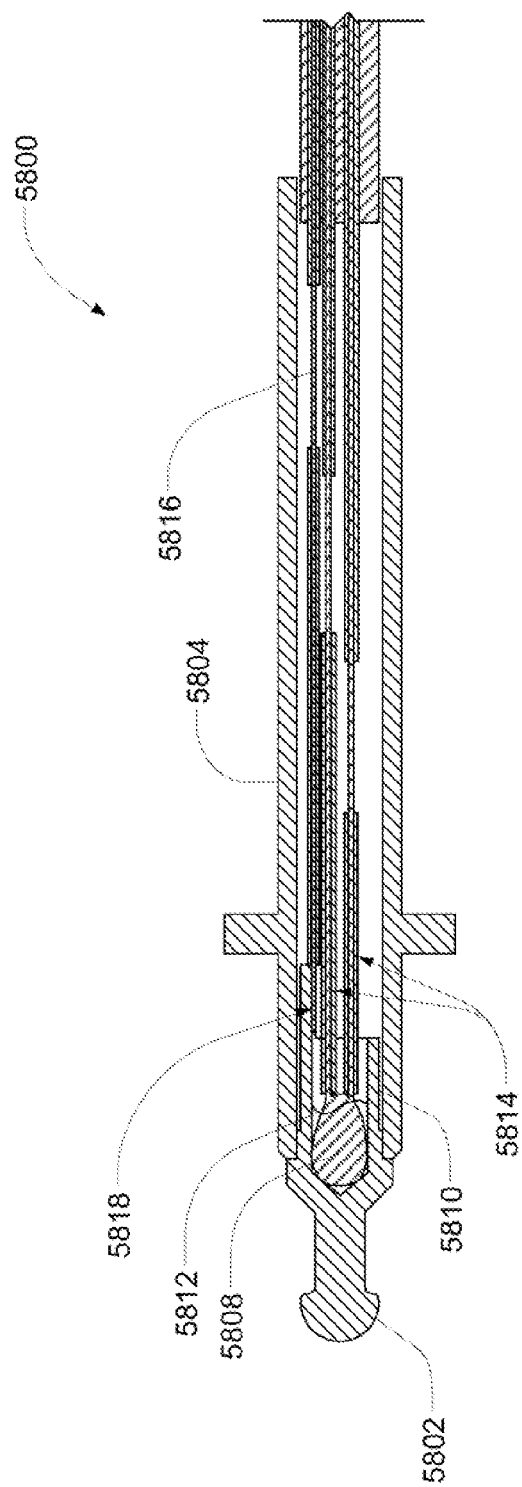
FIG. 20 is a section side view of one embodiment of the sensing probe.

Referring now to FIG. 20, a sectional view of an exemplary embodiment of a sensing probe 5800 is shown. The housing 5804 is a hollow structure that attaches to the tip 5802. The tip is made of a highly thermally conductive material. The housing 5804, in the exemplary embodiment, is made from a thermally insulative material. In some embodiments, the housing is made of a thermally and electrically insulative material. In the exemplary embodiment, the housing 5804 is made of plastic which is a thermally insulative and electrically insulative material. The tip 5802 either contacts the dialysate directly, or else is mated with a thermal well.

In the exemplary embodiment, the tip 5802 is attached to the housing 5804 using a urethane resin or another thermal insulator in between (area 5807) the tip 5802 and the housing 5804. Urethane resin additionally adds structural support. In alternate embodiments, other fabrication and joining methods can be used to join the tip 5802 to the housing 5804.

The tip 5802 of the sensing probe 5800 is made of a thermally conductive material. The better thermally conductive materials, for example, copper, silver and steel, can be used, however, depending on the desired use for the sensing probe and the dialysate; the materials may be selected to be durable and compatible for the intended use. Additionally, factors such as cost and ease of manufacture may dictate a different material selection. In one exemplary embodiment, the tip 5802 is made from copper. In other embodiments, the material can be an alloy of copper or silver, or either solid or an alloy of any thermally conductive material or element, including but not limited to metals and ceramics. However, in the exemplary embodiments, the tip 5802 is made from metal.

In the exemplary embodiment, the tip 5802 is shaped to couple thermally with a thermal well as described in the exemplary embodiment of the thermal well above. In the exemplary embodiment as well as in other embodiments, the tip 5802 may be shaped to insulate the thermal sensor 5808 from the ambient. In the exemplary embodiment, the tip 5802 is made from metal.

In alternate embodiments a non-electrically conductive material is used for the tip. These embodiments may be preferred for use where it is necessary to electrically insulate the thermal well from the probe. In another alternate embodiment, the tip 5802 may be made from any thermally conductive ceramic.

In the exemplary embodiment, the thermal sensor 5808 is located in the housing and is attached to the interior of the tip 5802 with a thermally conductive epoxy 5812. In the exemplary embodiment, the epoxy used is THERMALBOND, however, in other embodiments; any thermal grade epoxy can be used. However, in alternate embodiments, thermal grease may be used. In alternate embodiments, an epoxy or grease is not used.

The thermal sensor 5808, in the exemplary embodiment, is a thermistor. The thermistor generally is a highly accurate embodiment. However in alternate embodiments, the thermal sensor 5808 can be a thermocouple or any other temperature sensing device. The choice of thermal sensor 5808 may again relate to the intended use of the sensing apparatus.

Figure 21:
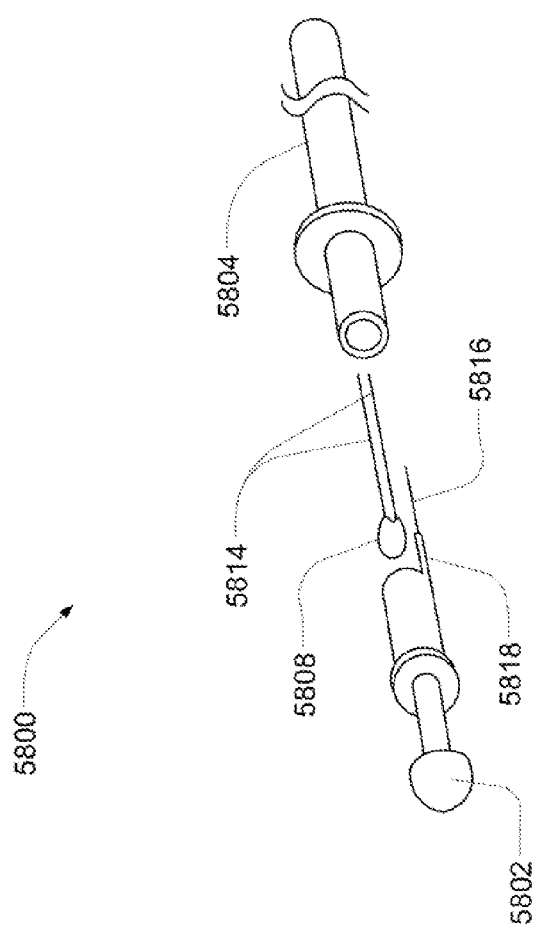
FIG. 21 is an exploded view of the embodiment shown in FIG. 8.

Leads 5814 from the thermal sensor 5808 exit the back of the housing 5804. These leads 5814 attach to other equipment used for calculations. In the exemplary embodiment, a third lead 5816 from the tip 5802 is also included. This third lead 5816 is attached to the tip on a tab 5818. The third lead 5816 is attached to the tip 5802 because in this embodiment, the tip 5802 is metal and the housing is plastic. In alternate embodiments, the housing 5804 is metal, thus the third lead 5816 may be attached to the housing 5804. Thus, the tip 5802, in the exemplary embodiment, includes a tab 5818 for attachment to a lead. However, in alternate embodiments, and perhaps depending on the intended use of the sensing apparatus, the third lead 5816 may not be included. Also, in alternate embodiments where a third lead is not desired, the tip 5802 may not include the tab 5818. Referring now to FIG. 21, an exploded view of the sensing probe 5800 is shown.

Figure 22:
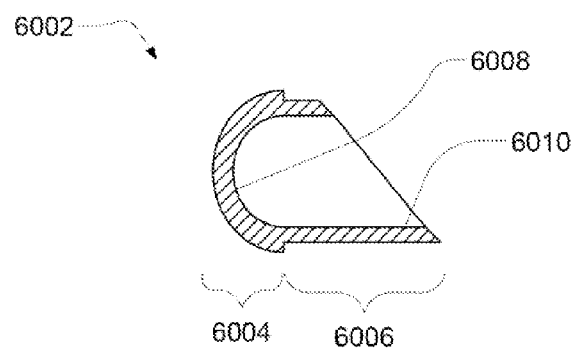
FIG. 22 is a sectional view of an alternate embodiment of the tip of the sensing probe.

Referring now to FIG. 22 an alternate embodiment of the exemplary embodiment is shown. In this embodiment, the tip 6002 of the sensing probe is shown. The tip 6002 includes a zone 6004 that will contact either a dialysate to be tested or a thermal well. A zone 6006 attaches to the sensor probe housing (not shown). An interior area 6008 accommodates the thermal sensor (not shown). In this embodiment, the tip 6002 is made from stainless steel. However, in other embodiments, the tip 6002 can be made from any thermally conductive material, including but not limited to: metals (including copper, silver, steel and stainless steel), ceramics or plastics.

Figure 23:
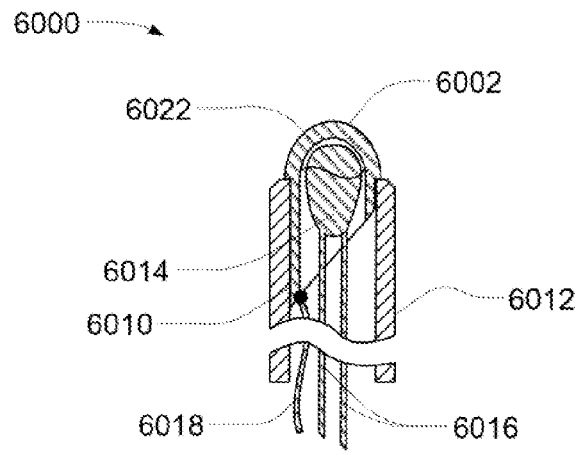
FIG. 23 is an alternate embodiment of the sensing probe.
Figure 24:
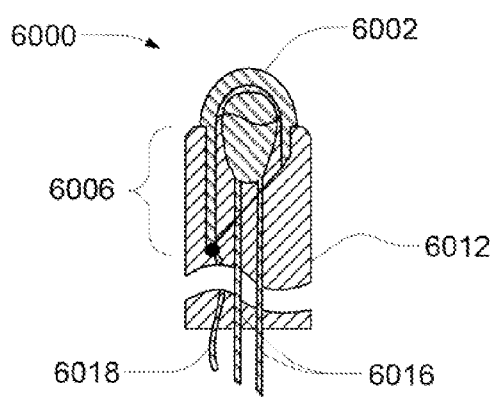
FIG. 24 is an alternate embodiment of the sensing probe.

In the exemplary embodiment, zone 6006 includes a tab 6010. A third lead (as described with respect to FIG. 20, 5816) attaches from the tab 6010. Referring next to FIGS. 23 and 24, the sensing probe 6000 is shown including the tip 6002 and the housing 6012. In one embodiment, the housing 6012 is made from any thermally insulative material, including but not limited to, plastic. In one embodiment the housing 6012 is press fit to the tip 6002, glued or attached by any other method. In one embodiment, the thermal sensor 6014 is thermally coupled to the tip 6002 with thermal grade epoxy or, in alternate embodiments, thermal grease 6022. Two leads 6016 from the thermal sensor 6014 extend to the distal end of the housing. In some embodiments, a third lead 6018 is attached to the tip 6002 from the tab 6010. As discussed above, in some embodiments where the third lead is not desired, the tip 6002 does not include a tab 6010.

Referring now to FIG. 24, an alternate embodiment of the sensing probe 6000 is shown. In this embodiment, the housing 6012 is a plastic molded over zone 6006 of the tip 6002 and the leads 6016, and in some embodiments, a third lead 6018.

Figure 25:
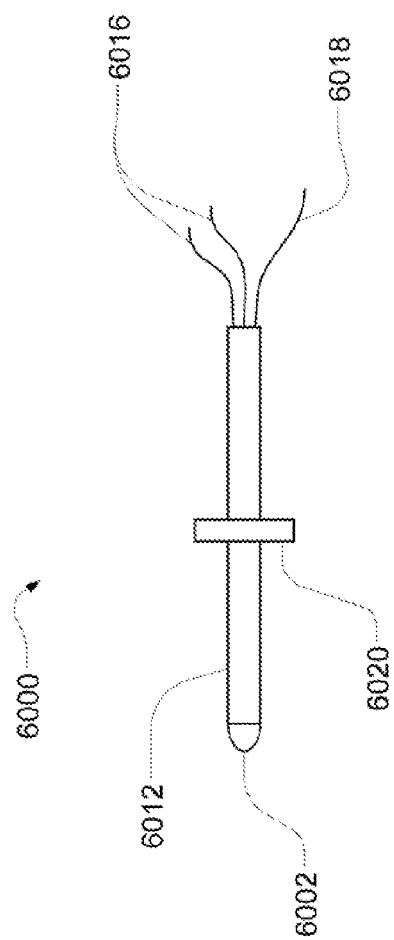
FIG. 25 is a side view of an alternate embodiment of the sensing probe.

Referring now to FIG. 25, a full side view of one embodiment of the sensing probe 6000. The sensing probe 6000 includes a housing 6012, a tip 6002 and the leads 6016, 6018. Flange 6020 is shown. In some embodiment, flange 6020 is used to mount and/or attachment to equipment.

Figure 26:
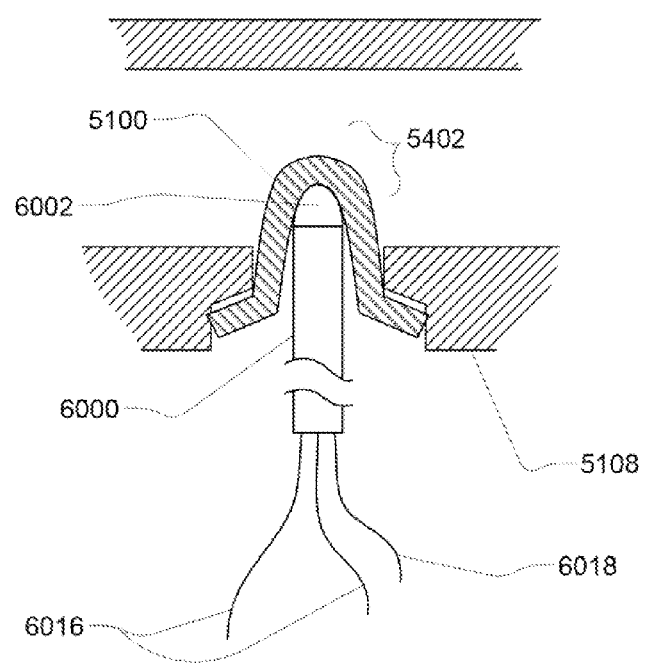
FIG. 26 is a section view of a sensing probe coupled to a thermal well.
Figure 27:
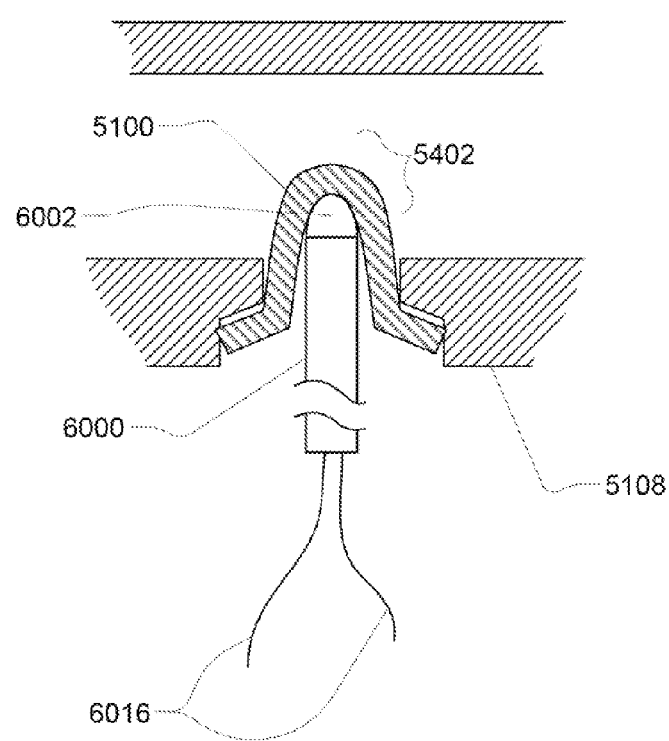
FIG. 27 is an alternate embodiment of the sensing probe.

Referring now to FIG. 26, the sensing probe 6000 is shown coupled to a thermal well 5100 which is fastened into a fluid line 5108. In the embodiment as shown, two leads 6016 are shown at the distal end of the sensing probe 6000. And, in some embodiments, a third lead 6018 is also incorporated into the sensing probe 6000. FIG. 27 shows an alternate embodiment where the sensing probe 6000 includes two leads 6016 but does not include the third lead 6018.

Referring flow to both FIGS. 26 and 27, the tip 6002 of the sensing probe 6000 is in direct contact with the thermal well 5100 which includes a zone 5402. The thermal well 5100 is hollow, and the inner part of zone 5402 is formed such that it will be in mating contact with the sensing probe tip 6002. As shown in this embodiment, the thermal well 5100 is designed to have a mating geometry with the sensing probe 6000. Thus, the geometry of the thermal well 5100 may depend on the geometry of the tip 6002 of the sensing probe 6000 and vice-versa. In some embodiments, it may be desirable that the sensing probe 6000 does not have a tight fit or a perfect mate with the thermal well 5100.

Figure 29:
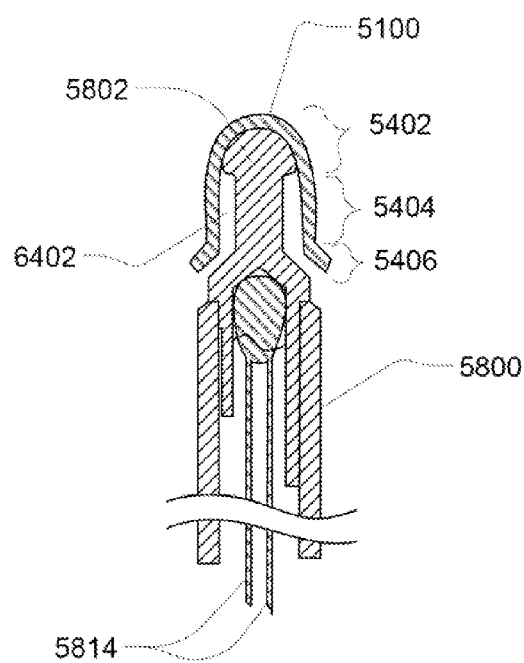
FIG. 29 is an alternate embodiment of the sensing probe shown in FIG. 14A.

Referring now to FIG. 28, one embodiment of the sensing probe 5800 is shown coupled to a thermal well 5100 which is fastened into a fluid line 5108. In the embodiment as shown, two leads 5814 are shown at the distal end of the sensing probe 5800. In some embodiments, a third lead 5816 is also incorporated into the sensing probe 5800. FIG. 29 shows an alternate embodiment where the sensing probe 5800 includes two leads 5814 but does not include the third lead 5816.

Referring now to both FIGS. 28 and 29, the tip 5802 of the sensing probe 5800 is in direct contact with the thermal well 5100, which includes a zone 5402. The thermal well 5100 is hollow, and the inner part of zone 5402 is formed such that it will be in mating contact with the sensing probe tip 5802. As shown in this embodiment, the thermal well 5100 is designed to have a mating geometry with the sensing probe 5800. Thus, the geometry of the thermal well 5100 depends on the geometry of the tip 5802 of the sensing probe 5800 and vice-versa.

6. Sensor Apparatus and Sensor Apparatus Systems

Figure 30:
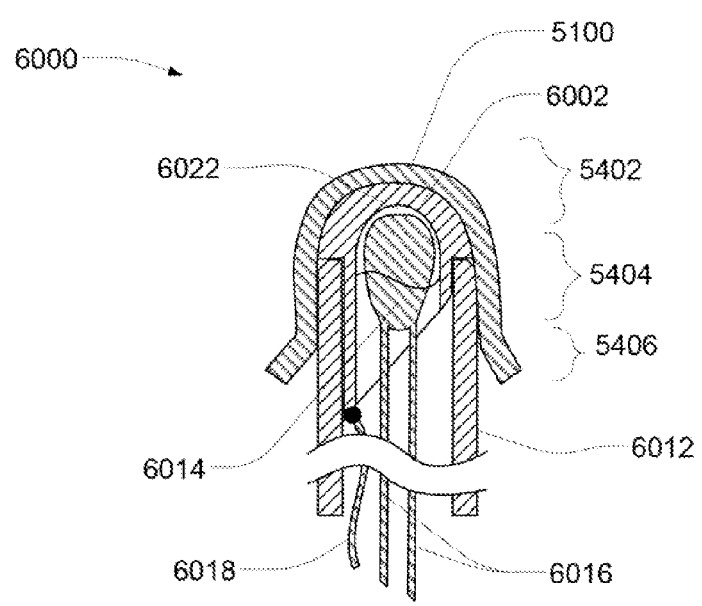
FIG. 30 is a sectional view of one exemplary embodiment of the sensor apparatus.

For purposes of description of the sensor apparatus, the sensor apparatus is described with respect to exemplary embodiments. The exemplary embodiments are shown in FIGS. 26, 27, and FIG. 30, with alternate exemplary embodiments in FIGS. 28 and 29. In alternate embodiments of the sensor apparatus, the sensing probe can be used outside of the thermal well. However, the sensor apparatus has already been described herein alone. Thus, the description that follows describes one embodiment of the exemplary embodiment of the sensor apparatus which includes, for this purpose, a sensing probe and a thermal well.

Alternate embodiments of thermal wells are described, often in relation to a fluid line. In most embodiments, the fluid line could be the fluid path of a cassette, such as fluid path 2303 of exemplary cassette 2300, described above. Alternatively, the principles described below could also be applicable to any of the cassette embodiment described herein.

Referring now to FIG. 30, in an exemplary embodiment, the sensing probe 6000 shown in FIG. 13A and the thermal well 5100 are shown coupled and outside of a fluid line. As described above, the thermal well 5100 can be in a fluid line, a protective sleeve, any disposable, machine, chamber, cassette or container. However, for purposes of this description of the exemplary embodiment, the thermal well 5100 is taken to be anywhere where it is used to determine thermal and/or conductive properties of a dialysate.

A dialysate is in contact with the outside of zone 5402 of the thermal well 5100. Thermal energy is transferred from the dialysate to the thermal well 5100 and further transferred to the tip 6002 of the sensing probe 6000. Thermal energy is then conducted to the thermal sensor 6014. The thermal sensor 6014 communicates via leads 6016 with equipment that can determine the temperature of the dialysate based on feedback of the thermal sensor 6014. In embodiments where conductivity sensing is also desired, lead 6018 communicates with equipment that can determine the conductivity of the dialysate. With respect to determining the conductivity of the dialysate, in addition to the lead 6018, a second electrical lead/contact (not shown) would also be used. The second lead could be a second sensor apparatus as shown in FIG. 30, or, alternatively, a second probe that is not necessarily the same as the sensor apparatus shown in FIG. 30, but rather, any probe or apparatus capable of sensing capacitance of the dialysate, including, an electrical contact.

Heat transfer from the tip 6002 to the thermal sensor 6014 may be improved by the use of a thermal epoxy or thermal grease 6022.

Referring now to FIGS. 28 and 29, in the alternate exemplary embodiment, whilst the sensing probe 5800 is coupled to the thermal well 5100, the tip 5802, having the geometry shown, forms an air gap 6402 between the inner zones 5404 and 5406 of the thermal well 5100 and the tip 5802. The air gap 6402 provides an insulative barrier so that only the top of the sensing tip of 5802 is in communication with the top zone 5402 of the thermal well 5100.

The sensing probe 5800 and thermal well 5100 are shown coupled and outside of a fluid line. As described above, the thermal well 5100 can be in a fluid line, a protective sleeve, disposable unit, machine, non-disposable unit, chamber, cassette or container. However, for purposes of this description of the exemplary embodiment, the thermal well 5100 is taken to be anywhere where it is used to determine thermal and/or conductive properties (FIG. 28) of a dialysate.

A dialysate is in contact with the outside of zone 5402 of the thermal well 5100. Thermal energy is transferred from the dialysate to the thermal well 5100 and further transferred to the tip 5802 of the sensing probe 5800. Thermal energy is then conducted to the thermal sensor 5808. The thermal sensor 5808 communicates via leads 5814 with equipment that can determine the temperature of the dialysate based on feedback of the thermal sensor 5808. In embodiments where conductivity sensing is also desired, lead 5816 communicates with equipment that can determine the conductivity of the dialysate. With respect to determining the conductivity of the dialysate, in addition to the lead 5816, a second electrical lead (not shown) would also be used. The second lead could be a second sensor apparatus as shown in FIG. 28, or, alternatively, a second probe that is not necessarily the same as the sensor apparatus shown in FIG. 28, but rather, any probe or apparatus capable of sensing capacitance of the dialysate, including, an electrical contact.

Heat transfer from the tip 5802 to the thermal sensor 5808 can be improved by the use of a thermal epoxy or thermal grease 5812.

Figure 31:
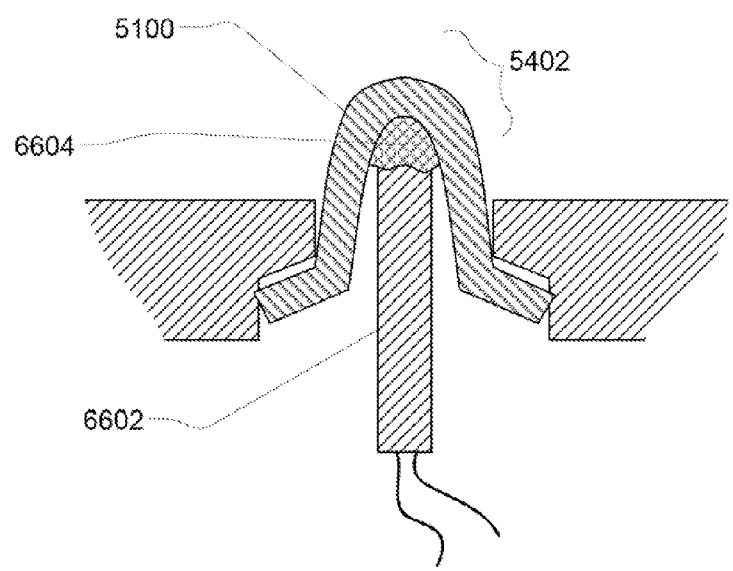
FIG. 31 shows an alternate embodiment of a sensing probe coupled to a thermal well.

Referring now to FIG. 31, an alternate embodiment showing a sensing probe 6602 coupled to a thermal well 5100 is shown. For purposes of this description, any embodiment of the sensing probe 6602 and any embodiment of the thermal well 5100 can be used. In this embodiment, to increase the thermal coupling between the tip of the sensing probe 6602 and the thermal well 5100, thermal grease 6604 is present at the interface of the tip of the sensing probe 6602 and the inner zone 5402 of the thermal well 5100. In one embodiment, the amount of thermal grease 6604 is a volume sufficient to only be present in zone 5402. However, in alternate embodiments, larger or smaller volumes of thermal grease can be used.

Figure 32:
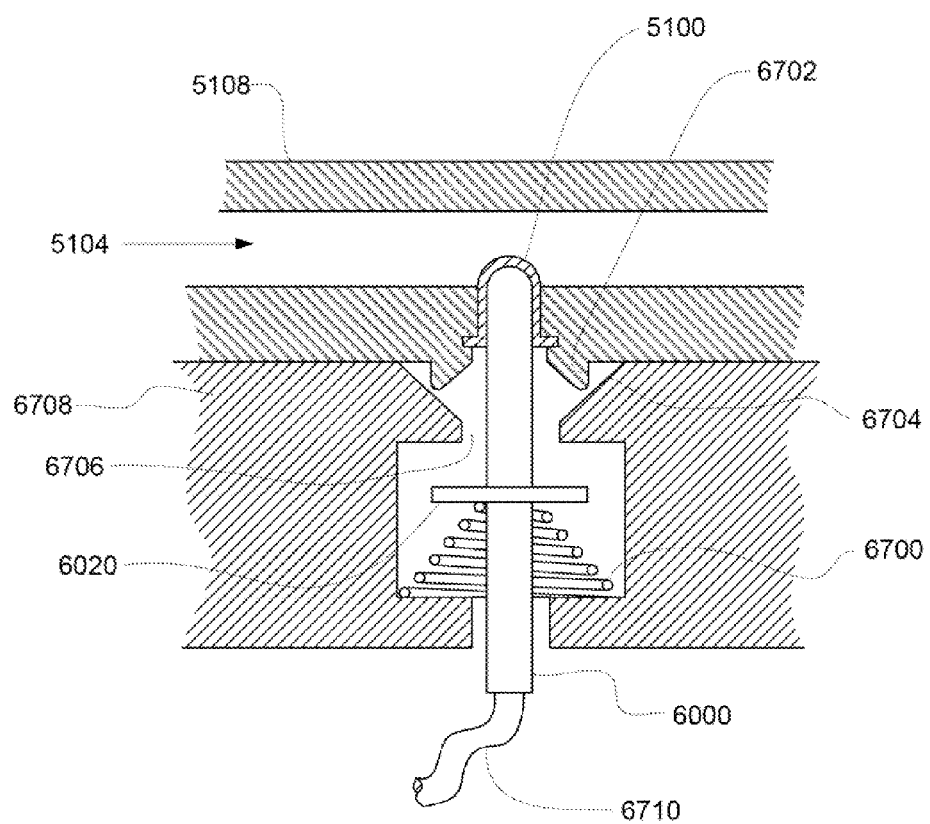
FIG. 32 is a section view of one embodiment of a sensing probe coupled to a thermal well and suspended by a spring.

Referring now to FIG. 32, a sensor apparatus system is shown. In the system, the sensor apparatus is shown in a device containing a fluid line 5108. The sensor apparatus includes the sensing probe 6000 and the thermal well 5100. In this embodiment, the thermal well 5100 and fluid line 5108 is a disposable portion and the sensing probe 6000 is a reusable portion. Also in the reusable portion is a spring 6700. The spring 6700 and sensing probe 6000 are located in a housing 6708. The housing 6708 can be in any machine, container, device or otherwise. The spring 6700 can be a conical, a coil spring, wave spring, or urethane spring.

In this embodiment, the thermal well 5100 and the sensing probe 6000 may include alignment features 6702, 6704 that aid in the thermal well 5100 and sensing probe 6000 being aligned. The correct orientation of the thermal well 5100 and the sensing probe 6000 may aid in the mating of the thermal well 5100 and the sensing probe 6000 to occur. The configuration of the space 6706 provides the sensing probe 6000 with space for lateral movement. This allows the sensing probe 6000 to, if necessary; move laterally in order to align with the thermal well 5100 for mating.

The sensing probe 6000 is suspended by a spring 6700 supported by the flange 6020. The spring 6700 allow vertical movement of the sensing probe 6000 when the thermal well 5100 mates with the sensing probe 6000. The spring 6700 aids in establishing full contact of the sensing probe 6000 and the thermal well 5100.

The fluid line 5108 can be in any machine, container, device or otherwise. The fluid line 5108 contains a fluid path 5104. A dialysate flows through the fluid path 5104 and the thermal well 5100, located in the fluid line 5108 such that the thermal well 5100 has ample contact with the fluid path 5104 and can sense the temperature properties and, in some embodiments, the conductive properties of the dialysate. The location of the thermal well 5100 in the fluid path 5104, as described in more detail above, may be related to the desired accuracy, the dialysate and other considerations.

The spring 6700 and sensing probe 6000 assembly, together with the space 6706 in the housing 6708 may aid in alignment for the mating of the sensing probe 6000 and the thermal well 5100. The mating provides the thermal contact so that the thermal well 5100 and the sensing probe 6000 are thermally coupled.

A wire 6710 is shown. The wire contains the leads. In some embodiments, there are two leads. Some of these embodiments are temperature sensing. In other embodiments, the wire contains three or more leads. Some of these embodiments are for temperature and conductivity sensing.

Figure 33:
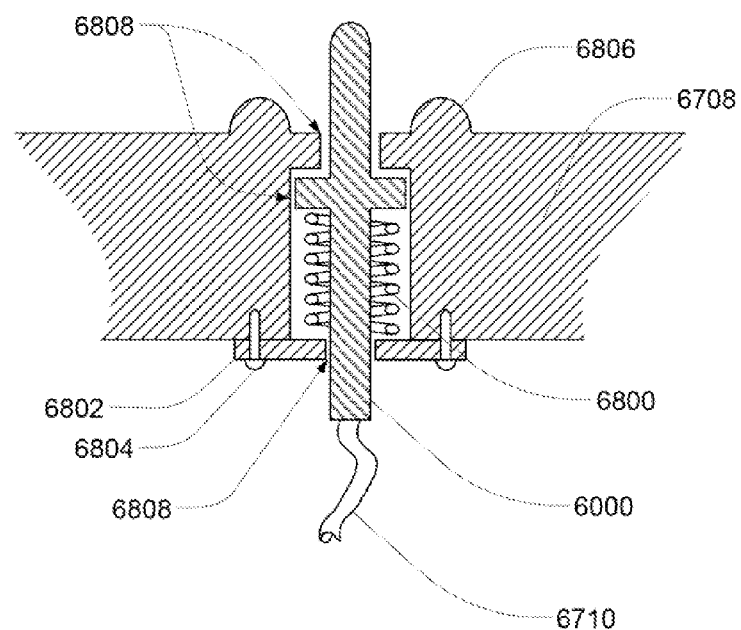
FIG. 33 is a section view of one embodiment of a sensing probe in a housing.

Referring now to FIG. 33, an alternate embodiment of the system shown in FIG. 17 is shown. In this embodiment, the sensing probe 6000 is suspended by a coil spring 6800. A retaining plate 6802 captures the coil spring 6800 to retain the spring 6800 and sensing probe 6000. In one embodiment, the retaining plate 6802 is attached to the housing 6708 using screws. However, in alternate embodiments, the retaining plate 6802 is attached to the housing 6708 using any fastening method including but not limited to: adhesive, flexible tabs, press fit, and ultrasonic welding. Aligning features 6806 on the housing 6708 aid in alignment of the sensing probe 6000 to a thermal well (not shown). Lateral movement of the sensing probe 6000 is provided for by clearance in areas 6808 in the housing 6708. A wire 6710 is shown. The wire contains the leads. In some embodiments, there are two leads. Some of these embodiments are temperature sensing. In other embodiments, the wire contains three or more leads. Some of these embodiments are for temperature and conductivity sensing.

Figure 34:
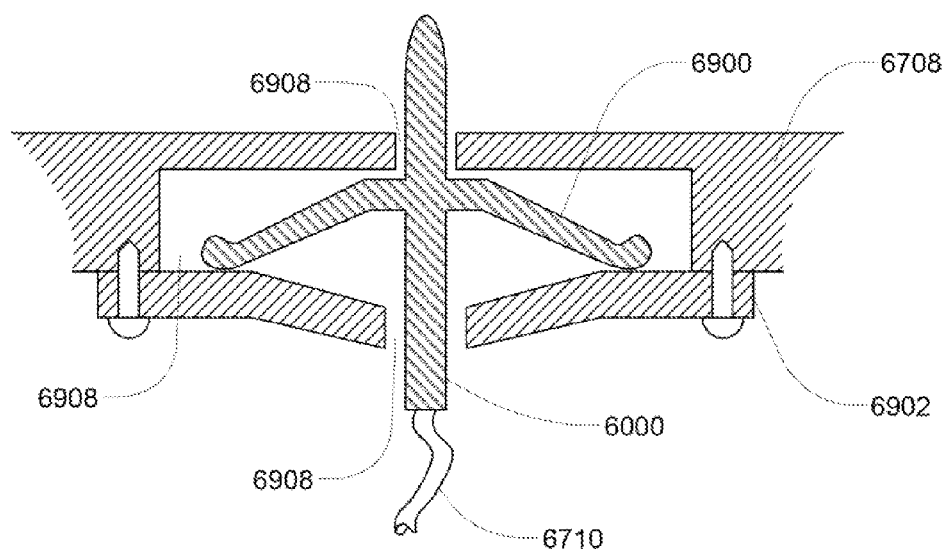
FIG. 34 is a section view of one embodiment of a sensing probe in a housing.

Referring now to FIG. 34, a sensing probe 6000 is shown in a housing 6708. In these embodiments, an alternate embodiment of a spring, a flexible member 6900, is integrated with the sensing probe 6000 to allow vertical movement of the sensing probe 6000 within the housing 6708. A retaining plate 6902 captures the flexible member 6900 to retain the flexible member 6900 and sensing probe 6000. In one embodiment, the retaining plate 6902 is attached to the housing 6708 using screws. However, in alternate embodiments, the retaining plate 6902 is attached to the housing 6708 using any fastening method including but not limited to: adhesive, flexible tabs, press fit, and ultrasonic welding. Lateral movement of the sensing probe 6000 is provided for by clearance in areas 6908 in the housing 6708. A wire 6710 is shown. The wire contains the leads. In some embodiments, there are two leads. Some of these embodiments are temperature sensing. In other embodiments, the wire contains three or more leads. Some of these embodiments are for temperature and conductivity sensing.

Figure 35:
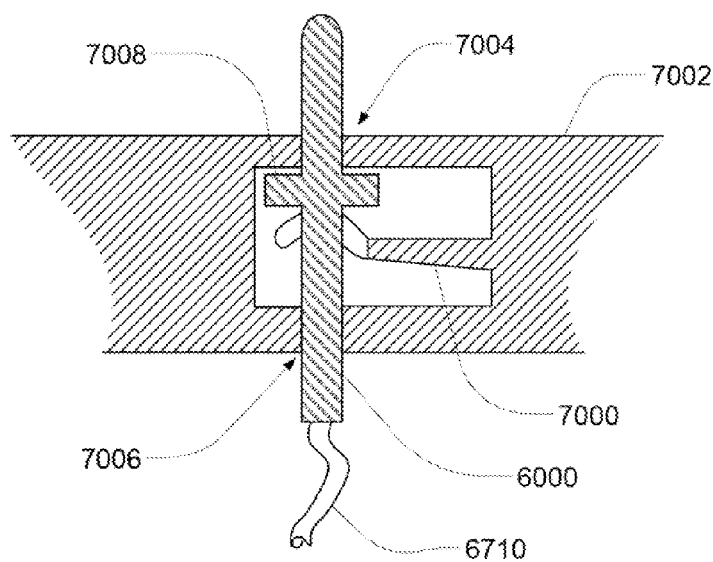
FIG. 35 is a section view of one embodiment of a sensing probe in a housing.

Referring now to FIG. 35, an alternate embodiment of a sensing probe 6000 in a housing 7002 is shown. In this embodiment, flexible member 7000 is attached or part of the housing 7002, provides for vertical movement of the sensing probe 6000. In this embodiment, the openings 7004, 7006 in housing 7002 are sized such that the sensing probe 6000 experiences limited lateral movement. Flexible member 7000 acts on the flange 7008 on the sensing probe 6000. A wire 6710 is shown. The wire contains the leads. In some embodiments, there are two leads. Some of these embodiments are temperature sensing. In other embodiments, the wire contains three or more leads. Some of these embodiments are for temperature and conductivity sensing.

The flange, as shown and described with respect to FIG. 35, can be located in any area desired on the sensing probe 6000. In other embodiments, the sensing probe may be aligned and positioned by other housing configurations. Thus, the embodiments of the housing shown herein are only some embodiments of housings in which the sensor apparatus can be used. The sensor apparatus generally depends on being located amply with respect to the dialysate. The configurations that accomplish this can vary depending on the dialysate and the intended use of the sensing apparatus. Further, in some embodiments where the thermal well is not used, but rather, the sensing probe is used only. The housing configurations may vary as well.

The sensing apparatus, in some embodiments, is used to sense conductivity. In some embodiments, this is in addition to temperature sensing. In those embodiments where both temperature and conductivity sensing is desired, the sensing probe typically includes at least three leads, where two of these leads may be used for temperature sensing and the third used for conductivity sensing.

Referring now to FIG. 15, for conductivity sensing, at least two sensors 7102, 7104 are located in an area containing the dialysate. In the embodiment shown, the area containing the dialysate is a fluid path 5104 inside a fluid line 5108. The conductivity sensors 7102, 7104 can be one of the various embodiments of sensing probes as described above, or one of the embodiments of the sensor apparatus embodiments (including the thermal well) as described above. However, in other embodiments, only one of the sensors is one of the embodiments of the sensor apparatus or one of the embodiments of the sensing probe, and the second sensor is any electrical sensor known in the art. Thus, in the systems described herein, conductivity and temperature can be sensed through using either one of the sensor apparatus or one of the sensor probes as described herein and a second capacitance sensor, or one of the sensor apparatus or one of the sensor probes as described herein and an electrical sensor.

Figure 36:
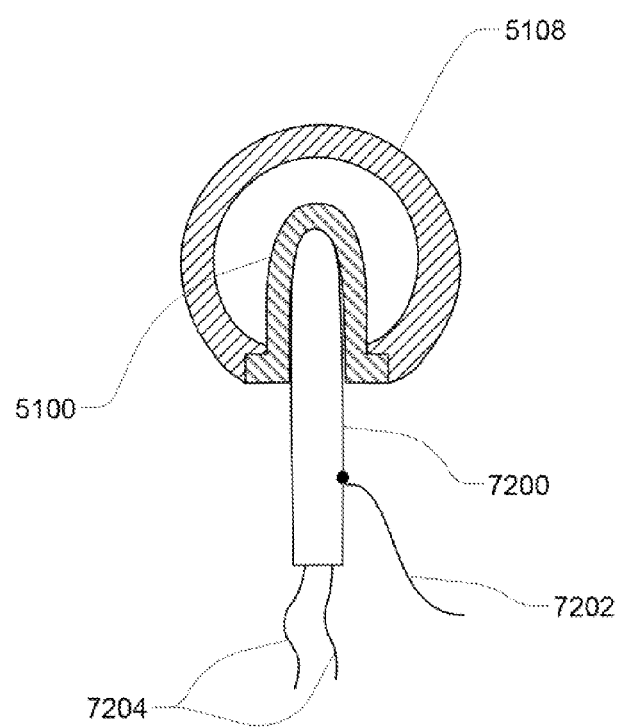
FIG. 36 is a section view of a fluid line with a sensor apparatus.

Referring now to FIG. 36, an alternate embodiment of a sensor apparatus including a sensing probe 7200 and a thermal well 5100 is shown in a fluid line 5108. In this embodiment, the sensing probe 7200 is constructed of a metal housing. The thermal well 5100 is also constructed of metal. The thermal well 5100 and the sensing probe 7200 can be made from the same metal or a different metal. The metal, in the preferred embodiment, is a conductive metal, which may include stainless steel, steel, copper and silver. A lead 7202 is attached to the sensing probe 7200 housing for conductivity sensing. The thermal sensing leads 7204 are attached to a thermal sensor located inside the sensing probe 7200 housing. In this embodiment, therefore, the third lead 7202 (or the lead for conductivity sensing) can be attached anywhere on the sensing probe 7200 because the sensing probe 7200 is constructed of metal. In the previously described embodiments, where the sensing probe housing was constructed of plastic, and the sensing tip constructed of metal, the third lead for conductivity sensing was attached to the sensing tip.

A known volume of dialysate may be used to determine conductivity. Thus, two sensors may be used and the volume of fluid between the two sensors can be determined. Conductivity sensing is done with the two electrical contacts (as described above), where one or both can be the sensor apparatus. The volume of dialysate between the two contacts is known.

Conductivity sensing is done by determining the conductivity from each of the sensors and then determining the difference. If the difference is above a predetermined threshold, indicating an abnormal difference in conductivity between the first and second sensor (the designations "first" and "second" being arbitrary), then it can be inferred that air may be trapped in the dialysate and a bubble detection alarm may be generated to indicate a bubble. Thus, if there is a large decrease in conductivity (and likewise, a large increase in resistance) between the first and second sensor, air could be trapped and bubble presence may be detected.

Leaks in a machine, system, device or container may be determined using the conductivity sensing. Where a sensing apparatus is in a machine, device or system, and that sensing apparatus senses conductivity, in one embodiment, a lead from the sensor apparatus (or electrical contacts) to an analyzer or computer machine may be present.

In some embodiments, the analyzer that analyzes the electrical signals between the contacts is connected to the metal of the machine, device, system or container. If the analyzer senses an electrical signal from the machine, then a fluid leak may be inferred.

The cassette embodiments shown and described in this description include exemplary and some alternate embodiments. However, any variety of cassettes are contemplated that include similar or additional functionality. As well, the cassettes may have varying fluid paths and/or valve placement and may utilize pumping functions, valving functions, and/or other cassette functions. All of these embodiments are within the scope of the invention.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

We claim:

1. A method for determining temperature and conductivity of a dialysate in a peritoneal dialysis pump cassette, said pump cassette comprising a first region formed of a flexible membrane and a second region formed of a rigid material and not comprising a flexible membrane, said second region having at least two thermal wells formed in the rigid material and extending into a liquid flow path in the cassette, at least one of said thermal wells having at least a portion comprising an electrically conductive material configured for contacting a liquid contained in said liquid flow path, said method comprising the steps of:
    placing the cassette in a dialysis machine having at least two sensing probes, each sensing probe adapted to mate with one of the thermal wells;
        thermally coupling each thermal well with a sensing probe such that temperature and conductivity can be determined;
        transferring thermal and conductivity signals through at least 3 leads from at least one of said sensing probes; and
        determining temperature and conductivity of a liquid contained in the liquid flow path using said signals.

2. The method of claim 1, wherein the pump cassette comprises a first side comprising the first region formed of the flexible membrane, a second side opposite the first side, and a third side comprising the second region having the at least two thermal wells.

3. A method for determining the temperature and conductivity of dialysate in a peritoneal dialysis pump cassette, said pump cassette comprising a first region formed of a flexible membrane and a second region formed of a rigid material and not comprising a flexible membrane, said second region having at least two thermal wells formed in the rigid material and extending into a liquid flow path in the cassette, at least one of said thermal wells having at least a portion comprising an electrically conductive material configured for contacting a liquid contained in said liquid flow path, said method comprising the steps of:
    placing the cassette in a dialysis machine having at least two sensing probes, each sensing probe adapted to mate with one of the thermal wells;
    thermally coupling each thermal well with a sensing probe such that temperature and conductivity can be determined;
    transferring thermal and conductivity signals through at least 3 leads from at least one of said sensing probes;
    determining temperature and conductivity of a liquid contained in the liquid flow path using said signals; and
    comparing the conductivity determined to a preset conductivity level.

4. A method according to claim 3, wherein said method further comprises the step of sending a signal to the dialysis machine if the determined conductivity is not within a specified range of the preset conductivity level.

5. A method according to claim 4, wherein said method further comprises the step of suspending peritoneal dialysis treatment if the determined conductivity is not within the specified range of the preset conductivity level.

6. The method of claim 3, wherein the pump cassette comprises a first side comprising the first region formed of the flexible membrane, a second side opposite the first side, and a third side comprising the second region having the at least two thermal wells.

7. A disposable pump cassette for performing peritoneal dialysis comprising:
    a) a first side comprising a flexible membrane for pumping or directing liquid in the cassette;
    b) an opposing second side adapted and configured to receive a force urging at least a portion of the cassette against the flexible membrane when the cassette is mounted in a dialysis machine; and c) a third side not comprising a flexible membrane, wherein at least a portion of said third side:
   is not parallel to said first side;
   is not parallel to said opposing second side;
   spans at least a portion of the distance separating said first side from said opposing second side; and
   comprises a thermal well extending into a liquid path in the cassette, wherein
   the thermal well has a liquid side for making contact with liquid in the cassette and an opposing probe side for reversible mating with a sensing probe, said thermal well being thermally conductive between the liquid side and the probe side.

8. A cassette according to claim 7, wherein the cassette comprises at least one pump chamber.

9. A cassette according to claim 7, wherein the cassette comprises at least one valving station.

10. A cassette according to claim 7, wherein the cassette comprises at least one pump chamber and one valving station.

11. A cassette according to claim 7, wherein the thermal well is a first thermal well, and the cassette comprises a second thermal well spaced apart from the first thermal well, wherein the liquid side of the first thermal well is in fluid communication with the liquid side of the second thermal well through a liquid flow path in the cassette.

12. A cassette according to claim 11, wherein the first thermal well can be reversibly coupled with a first sensing probe, the second thermal well can be reversibly coupled with a second sensing probe, and at least a portion of each thermal well is electrically conductive, said couplings permitting conductivity sensing of a liquid in the liquid flow path in the cassette.

13. A cassette according to claim 12, wherein at least one of the first sensing probe and the second sensing probe has three leads for transmitting thermal and electrical conductivity signals.

14. A cassette according to claim 7, wherein the well is secured to the cassette using at least one of press fit connection, flexible tabs, adhesive, ultrasonic weld, and a retaining plate with fastener.

15. A disposable pump cassette for performing peritoneal dialysis comprising:
   a) a first region formed of a flexible membrane; and
   b) a second region, not co-planar with said first region, that is formed of a rigid material, does not comprise a flexible membrane and has at least two thermal wells formed in the rigid material and extending into a liquid flow path in the cassette; wherein
   each thermal well has a liquid side for making contact with liquid in the cassette and an opposing probe side for reversible mating with a sensing probe, each thermal well being thermally conductive between the liquid side and the probe side.

16. A cassette according to claim 15, wherein the cassette comprises at least one pump chamber.

17. A cassette according to claim 15, wherein the cassette comprises at least one valving station.

18. A cassette according to claim 15, wherein the cassette comprises at least one pump chamber and one valving station.

19. A cassette according to claim 15, wherein the thermal wells are spaced apart from each other and wherein the liquid side of each thermal well is in fluid communication with the liquid side of each other thermal well through the liquid flow path in the cassette.

20. A cassette according to claim 19, wherein a first thermal well can be reversibly coupled with a first sensing probe, a second thermal well can be reversibly coupled with a second sensing probe, and at least a portion of each thermal well is electrically conductive, said couplings permitting conductivity sensing of a liquid in the liquid flow path.

21. A cassette according to claim 20, wherein at least one of the first sensing probe and the second sensing probe has three leads for transmitting thermal and electrical conductivity signals.

22. A cassette according to claim 15, wherein the at least two wells are secured to the cassette using at least one of press fit connection, flexible tabs, adhesive, ultrasonic weld, and a retaining plate with fastener.

* * * * *